(12) United States Patent
Raleigh et al.

(10) Patent No.: US 9,056,136 B2
(45) Date of Patent: Jun. 16, 2015

(54) WEAKLY BASIC 2-NITROIMIDAZOLES FOR THE NON-INVASIVE DETECTION OF TISSUE HYPOXIA

(75) Inventors: James A. Raleigh, Chapel Hill, NC (US); David Y-W Lee, Cambridge, MA (US); Xiaoshen Ji, Acton, MA (US)

(73) Assignee: Natural Pharmacia International, Inc., Burlington, MA (US)

( * ) Notice: Subject to any disclaimer, the term of this patent is extended or adjusted under 35 U.S.C. 154(b) by 1309 days.

(21) Appl. No.: 11/544,698

(22) Filed: Oct. 6, 2006

(65) Prior Publication Data

US 2008/0085237 A1    Apr. 10, 2008

(51) Int. Cl.
 A61K 51/00 (2006.01)
 A61M 36/14 (2006.01)
 A61K 49/10 (2006.01)
 A61K 51/04 (2006.01)

(52) U.S. Cl.
 CPC ............. A61K 49/10 (2013.01); A61K 51/0455 (2013.01); A61K 51/0459 (2013.01)

(58) Field of Classification Search
 CPC ... A61K 51/00; A61K 51/06; A61K 51/0497; A61K 51/0453; A61K 51/041; A61K 51/044; A61K 51/04; A61K 51/0455; A61K 51/0459; A61K 49/10; A61K 49/00; C07D 231/06; C07D 231/04; C07D 231/10; C07D 261/06; C07D 233/04; C07D 233/54; C07D 233/02; C07D 307/04; C07D 207/00; C07D 207/18; C07D 207/30; C07D 295/00; C07D 249/04; C07D 249/08; C07D 277/08; C07D 277/20; C07D 285/12; C07D 273/01; C07D 273/00; C07D 211/06; C07D 291/04; C07D 213/00; C07D 263/30; C07D 263/42; C07D 239/24; C07D 275/02; C07D 241/10; C07D 271/04; C07D 271/06; C07D 271/08; C07D 271/10; C07D 237/06
 USPC ........... 424/1.11, 1.65, 1.69, 1.81, 1.85, 1.89, 424/9.1, 9.2, 9.3, 9.4, 9.5, 9.6, 9.7, 9.8; 548/100, 300.1; 546/1; 568/300, 924; 534/7, 10–16
 See application file for complete search history.

(56) References Cited

U.S. PATENT DOCUMENTS

| | | | |
|---|---|---|---|
| 4,241,060 A | 12/1980 | Smithen | |
| 4,282,232 A | 8/1981 | Agrawal | |
| 4,927,941 A * | 5/1990 | Kagiya et al. | 548/264.8 |
| 5,086,068 A | 2/1992 | Raleigh et al. | |
| 5,387,692 A | 2/1995 | Riley et al. | |
| 5,674,693 A * | 10/1997 | Raleigh et al. | 435/7.23 |
| 5,721,265 A | 2/1998 | Tracy et al. | |
| 5,728,843 A | 3/1998 | Wallace et al. | |
| 7,842,278 B2 | 11/2010 | Lee et al. | |
| 2005/0026974 A1 | 2/2005 | Koch et al. | |
| 2008/0085237 A1 | 4/2008 | Raleigh et al. | |

FOREIGN PATENT DOCUMENTS

| | | |
|---|---|---|
| CN | 1729012 A | 2/2006 |
| EP | 0 302 416 | 2/1989 |
| WO | WO 88/08840 | 11/1988 |
| WO | WO 8808840 | * 11/1988 |
| WO | WO 01/07414 | 2/2001 |
| WO | WO 2008/063749 | 5/2008 |
| WO | WO 2008/070336 | 6/2008 |

OTHER PUBLICATIONS

Lewis, Sr., Hawley's Condensed Chemical Dictionary, Twelfth Edition (1993), 'Non-metal', p. 835.*
Albina et al., "HIF-1 Expression in Healing Wounds: HIF-1Alpha Induction in Primary Inflammatory Cells by TNF-Alpha," Am. J. Physiol. Cell. Physiol. 281: C1971-1977, 2001.
Arteel et al., "Acute Alcohol Produces Hypoxia Directly in Rat Liver Tissue In Vivo: Role of Kupffer Cells," Am. J. Physiol 271: G494-500, 1996.
Arteel et al., "Evidence That Hypoxia Markers Detect Oxygen Gradients in Liver: Pimonidazole and Retrograde Perfusion of Rat Liver," Br. J. Cancer 72: 889-895, 1995.
Badger et al., "The Immediate Effect of Castration on Female Rabbit Bladder Blood Flow and Tissue Oxygenation," Urol. Int. 76: 264-268, 2006.
Ballinger et al., "In Vitro and In Vivo Evaluation of a Technetium-99m-Labeled 2-Nitroimidazole (BMS181321) as a Marker of Tumor Hypoxia," J. Nucl. Med. 37: 1023-1031, 1996.
Bussink et al., "Changes in Blood Perfusion and Hypoxia After Irradiation of a Human Squamous Cell Carcinoma Xenograft Tumor Line," Radiat. Res. 153: 398-404, 2000.
Carnell et al., "An Immunohistochemical Assessment of Hypoxia in Prostate Carcinoma Using Pimonidazole: Implications for Radioresistance," Int. J. Radiat. Oncol. Biol. Phys. 65: 91-99, 2006.
Chapman et al., "A Marker for Hypoxic Cells in Tumours With Potential Clinical Applicability," Br. J. Cancer 43: 546-550, 1981.
Cheema et al., "Adventitial Microvessel Formation After Coronary Stenting and the Effects of SU11218, A Tyrosine Kinase Inhibitor," J. Am. Coll. Cardiol. 47: 1067-1075, 2006.
Cline et al., "Immunohistochemical Detection of a Hypoxia Marker in Spontaneous Canine Tumours," Br. J. Cancer 62: 925-931, 1990.
Couturier et al., "Fluorinated Tracers for Imaging Cancer with Positron Emission Tomography," Eur. J. Nucl. Med. Mol. Imaging 31: 1182-1206, 2004.
Damaser et al., "Effect of Vaginal Distension on Blood Flow and Hypoxia of Urogenital Organs of the Female Rat," J. Appl. Physiol. 98: 1884-1890, 2005.
Danielsson et al., "Phenytoin Teratogenicity: Hypoxia Marker and Effects on Embryonic Heart Rhythm Suggest an hERG-Related Mechanism," Birth Defects Res. (Part A) Clin. Mol. Teratol. 73: 146-153, 2005.

(Continued)

Primary Examiner — D L Jones
(74) Attorney, Agent, or Firm — Clark & Elbing LLP; Paul T. Clark, Esq.; Todd Armstrong

(57) ABSTRACT

The present invention incorporates weakly basic substituents (pKa about 8 or greater) such as pyrrolidine, piperidine, piperazine and azapane moieties in halogenated 2-nitroimidazoles for the non-invasive detection of cellular hypoxia in normal and malignant tissues. The compounds of the invention can be used in $^{18}F$ positron emission tomography, $^{19}F$ magnetic resonance spectroscopy, and $^{19}F$ magnetic resonance imaging.

52 Claims, 1 Drawing Sheet

(56) References Cited

OTHER PUBLICATIONS

Danylkova et al., "Histological and Morphometric Evaluation of Transient Retinal and Optic Nerve Ischemia in Rat," *Brain Res.* 1096: 20-29, 2006.
Dennis et al., "Cellular Uptake of Misonidazole and Analogues with Acidic or Basic Functions," *Int. J. Radiat. Biol.* 47: 629-643, 1985.
Dewhirst et al., "Temporal Changes in $PO_2$ of R3230AC Tumors in Fischer-344 Rats," *Int. J. Radial. Oncol. Biol. Phys.* 42: 723-726, 1998.
Dodd et al., "Osteocyte Hypoxia: A Novel Mechanotransduction Pathway," *Am. J. Physiol.* 277: C598-602, 1999.
Durand et al., "Identification of Nonproliferating but Viable Hypoxic Tumor Cells In Vivo," *Cancer Res.* 58: 3547-3550, 1998.
Evans et al., "Non Invasive Detection of Tumor Hypoxia Using the 2-Nitroimidazole [$^{18}$F]EF1," *J. Nucl. Med.* 41: 327-336, 2000.
Ghafar et al., "Effects of Chronic Partial Outlet Obstruction on Blood Flow and Oxygenation of the Rat Bladder," *J. Urol.* 167: 1508-1512, 2002.
Gross et al., "Calibration of Misonidazole Labeling by Simultaneous Measurement of Oxygen Tension and Labeling Density in Multicellular Spheroids," *Int. J. Cancer* 61: 567-573, 1995.
Hale et al., "Hypoxia in the Thymus: Role of Oxygen Tension in Thymocyte Survival," *Am. J. Physiol. Heart Circ. Physiol.* 282: H1467-1477, 2002.
Helmlinger et al., "Interstitial pH and $pO_2$ Gradients in Solid Tumors In Vivo: High-Resolution Measurements Reveal a Lack of Correlation," *Nature Medicine* 3: 177-182, 1997.
Hochachka, "Patterns of $O_2$-Dependence of Metabolism," *Adv. Exp. Med. Biol.* 222: 143-151, 1988.
Iyer et al., "A Dual Hypoxic Marker Technique for Measuring Oxygenation Change Within Individual Tumours," *Br. J. Cancer* 78: 163-169, 1998.
Jeong et al., "Hypoxia Potentiates Transforming Growth Factor-Beta Expression of Hepatocyte During the Cirrhotic Condition in Rat Liver," *Liver Int.* 24: 658-668, 2004.
Jin et al., "Dynamic Measurements of Hexafluoromisonidazole (CCI-103F) Retention in Mouse Tumours by $^1$H/$^{19}$F Magnetic Resonance Spectroscopy," *Int. J. Radiat. Biol.* 58: 1025-1034, 1990.
Kaanders et al., "Pimonidazole Binding and Tumor Vascularity Predict for Treatment Outcome in Head and Neck Cancer," *Cancer Res.* 62: 7066-7074, 2002.
Kaneta et al., "Imaging of Ischemic but Viable Myocardium Using a New $^{18}$F-Labeled 2-Nitroimidazole Analog, $^{18}$F-FRP170," *J. Nucl. Med.* 43: 109-116, 2002.
Kennedy et al., "Proliferation and Hypoxia in Human Squamous Cell Carcinoma of the Cervix: First Report of Combined Immunohistochemical Assays," *Int. J. Radial. Oncol. Biol. Phys.* 37: 897-905, 1997.
Kleiter et al., "A Comparison of Oral and Intravenous Pimonidazole in Canine Tumors Using Intravenous CCI-103F as a Control Hypoxia Marker," *Int. J. Radiat. Oncol. Biol. Phys.* 64: 592-602, 2006.
Koh et al., "Evaluation of Oxygenation Status During Fractionated Radiotherapy in Human Nonsmall Cell Lung Cancers Using [F-18] Fluoromisonidazole Positron Emission Tomography," *Int. J. Radiat. Oncol. Biol. Phys.* 33: 391-398, 1995.
Lee et al., "Determination of Hypoxic Region by Hypoxia Marker in Developing Mouse Embryos In Vivo: A Possible Signal for Vessel Development," *Dev. Dyn.* 220: 175-186, 2001.
Ljungkvist et al., "Changes in Tumor Hypoxia Measured with a Double Hypoxic Marker Technique," *Int. J. Radiat. Oncol. Biol. Phys.* 48: 1529-1538, 2000.
McKim et al., "Chronic Intragastric Alcohol Exposure Causes Hypoxia and Oxidative Stress in the Rat Pancreas," *Arch. Biochem. Biophys.* 417: 34-43, 2003.
Morani et al., "Lung Dysfunction Causes Systemic Hypoxia in Estrogen Receptor Beta Knockout (ERBeta$^{-/-}$) Mice," *Proc. Natl. Acad. Sci. USA* 103: 7165-7169, 2006.
Mount Desert Island Biological Laboratory, "Chemicals: Pimonidazole," *The Comparative Toxicogenomics Database*, 2004.
Nanka et al., "Experimental Hypoxia and Embryonic Angiogenesis," *Dev. Dyn.* 235: 723-733, 2006.
Olive et al., "Measuring Hypoxia in Solid Tumours—Is There a Gold Standard?" *Acta. Oncol.* 40:917-923, 2001.
Peters et al., "The Transcription Factors Hypoxia-Inducible Factor 1 Alpha and Ets-1 Colocalize in the Hypoxic Synovium of Inflamed Joints in Adjuvant-Induced Arthritis," *Arthritis Rheum.* 50: 291-296, 2004.
Raleigh et al., "An Enzyme-Linked Immunosorbent Assay for Hypoxia Marker Binding in Tumors," *Br. J. Cancer* 69: 66-71, 1994.
Raleigh et al., "Covalent Binding of a Fluorinated 2-Nitroimidazole to EMT-6 Tumors in Balb/C Mice: Detection by F-19 Nuclear Magnetic Resonance at 2.35 T," *Int. J. Radiat. Oncol. Biol. Phys.* 12: 1243-1245, 1986.
Raleigh et al., "Fluorescence Immunohistochemical Detection of Hypoxic Cells in Spheroids and Tumours," *Br. J. Cancer* 56: 395-400, 1987.
Raleigh et al., "Importance of Thiols in the Reductive Binding of 2-Nitroimidazoles to Macromolecules," *Biochem. Pharmacol.* 40: 2457-2464, 1990.
Raleigh et al., "Reductive Fragmentation of 2-Nitroimidazoles: Amines and Aldehydes," *Int. J. Radiat. Oncol. Biol. Phys.* 10: 1337-1340, 1984.
Raleigh, James, "Hypoxyprobe™-1," www.hypoxyprobe.com/headerrow.htm, 2006.
Rasey, et al., "Characterization of [$^{18}$F] Fluoroetanidazole, A New Radiopharmaceutical for Detecting Tumor Hypoxia," *J. Nucl. Med.* 40: 1072-1079, 1999.
Rasey et al., "Radiolabeled Fluoromisonidazole as an Imaging Agent for Tumor Hypoxia," *Int. J. Radiat. Oncol. Biol. Phys.* 17: 985-991, 1989.
Ross, "Increased Sensitivity of the Walker Tumour Towards Aromatic Nitrogen Mustards Carrying Basic Side Chains Following Glucose Pretreatment," *Biochem. Pharmacol.* 8: 235-240, 1961.
Saunders et al., "The Clinical Testing of Ro 03-8799—Pharmacokinetics, Toxicology, Tissue and Tumor Concentrations," *Int. J. Radiat. Oncol. Biol. Phys.* 10: 1759-1763, 1984.
Solomon et al., "Modulation of Intratumoral Hypoxia by the Epidermal Growth Factor Receptor Inhibitor Gefitinib Detected Using Small Animal PET imaging," *Mol. Cancer Ther.* 4: 1417-1422, 2005.
Sorger et al., "[$^{18}$F]Fluoroazomycinarabinofuranoside ($^{18}$FAZA) and [$^{18}$F]Fluoromisonidazole ($^{18}$FMISO); A Comparative Study of Their Selective Uptake in Hypoxic Cells and PET Imaging in Experimental Rat Tumors," *Nucl. Med. Biol.* 30: 317-326, 2003.
Strauss et al., "Nitroimidazoles for Imaging Hypoxic Myocardium," *J. Nucl. Cardiol.* 2: 437-435, 1995.
Thomlinson et al., "The Histological Structure of Some Human Lung Cancers and the Possible Implications for Radiotherapy," *Br. J. Cancer* 9: 539-549, 1955.
Thurman et al., "The Role of Gut-Derived Bacterial Toxins and Free Radicals in Alcohol-Induced Liver Injury," *J. Gastroenterol. Hepatol.* 13: S39-50, 1998.
Urtasun et al., "A Novel Technique for Measuring Human Tissue $pO_2$ at the Cellular Level," *Br. J. Cancer* 54: 453-457, 1986.
Varghese et al., "Hypoxia-Dependent Reduction of 1-(2-Nitro-1-Imidazolyl)-3-Methoxy-2-Propanol by Chinese Hamster Ovary Cells and KHT Tumor Cells In Vitro and In Vivo," *Cancer Res.* 36: 3761-3765, 1976.
Varia et al., "Pimonidazole: A Novel Hypoxia Marker for Complementary Study of Tumor Hypoxia and Cell Proliferation in Cervical Carcinoma," *Gynecol. Oncol.* 71: 270-277, 1998.
Vaupel et al., "Oxygenation Status of Malignant Tumors: Pathogenesis of Hypoxia and Significance for Tumor Therapy," *Semin. Oncol.* 28: 29-35, 2001.
Villanueva et al., "IschemicAcute Renal Failure Induces the Expression of a Wide Range of Nephrogenic Proteins," *Am. J. Physiol. Regul. Integr. Comp. Physiol.* 290: R861-870, 2006.
Wardman, "Molecular Structure and Biological Activity of Hypoxic Cell Radiosensitizers and Hypoxic-Specific Cytotoxins," in *Advanced Topics on Radiosensitizers of Hypoxic Cell*, 49-75, 1982.

(56) References Cited

OTHER PUBLICATIONS

Wouters et al., "Cells at Intermediate Oxygen Levels Can Be More Important Than the 'Hypoxic Fraction' in Determining Tumor Response to Fractionated Radiotherapy," *Radiat. Res.* 147: 541-550, 1997.
Yamamoto et al., "Synthesis and Evaluation of 4-Bromo-1-(3-[$^{18}$F]Fluoropropyl)-2-Nitroimidazole with Low Energy LUMO Orbital Designed as Brain Hypoxia-Targeting Imaging Agent," *Biol. Pharm. Bull.* 25: 616-621, 2002.
Yang et al., "Development of F-18-Labeled Fluoroerythronitroimidazole as a PET Agent for Imaging Tumor Hypoxia," *Radiology* 194: 795-800, 1995.
Ziemer et al., "Noninvasive Imaging of Tumor Hypoxia in Rats Using the 2-Nitroimidazole $^{18}$F-EF5," *Eur. J. Nucl. Med. Mol. Imaging* 30: 259-266, 2003.
Zhong et al., "Cyclosporin A Increases Hypoxia and Free Radical Production in Rat Kidneys: Prevention by Dietary Glycine," *Am. J. Physiol.* 275: F595-604, 1998.
Naylor et al., "Synthesis and Evaluation of Novel Electrophilic Nitrofuran Carboxamides and Carboxylates as Radiosensitizers and Bioreductively Activated Cytotoxins," *J. Med. Chem.* 33:2508-2513 (1990).
International Search Report for PCT/US2007/080062, mailed Jun. 4, 2008.
Ali et al., "Metal Complexes as Photo- and Radiosensitizers," *Chem. Rev.* 99: 2379-2450, 1999.
Barth et al., "Boron Neutron Capture Therapy for Cancer. Realities and Prospects," *Cancer* 70: 2995-3007, 1992.
Barth et al., "Boron Neutron Capture Therapy of Brain Tumors: An Emerging Therapeutic Modality," *Neurosurgery* 44: 433-450, 1999.
Barth et al., "Boron Neutron Capture Therapy of Cancer: Current Status and Future Prospects," *Clin. Cancer Res.* 11: 3987-4002, 2005.
Bonnett, "Photosensitizers of the Porphyrin and Phthalocyanine Series for Photodynamic Therapy," *Chem. Soc. Rev.* 24: 19-33, 1995.
Capala et al., "Accumulation of Boron in Malignant and Normal Cells Incubated in vitro with Boronophenylalanine, Mercaptoborane or Boric Acid," *Radiat. Res.* 146: 554-560, 1996.
Elowitz et al., "Biodistribution of p-Boronophenylalanine in Patients with Glioblastoma Multiforme for Use in Boron Neutron Capture Therapy," *Neurosurgery* 42: 463-469, 1998.
Gupta et al., "Common Challenges and Problems in Clinical Trials of Boron Neutron Capture Therapy of Brain Tumors," *J. Neurooncol.* 62: 197-210, 2003.
Hodgkiss, "Use of 2-Nitroimidazoles as Bioreductive Markers for Tumour Hypoxia," *Anticancer Drug Des.* 13: 687-702, 1998.
Kageji et al., "Pharmacokinetics and Boron Uptake of BSH ($Na_2B_{12}H_{11}SH$) in Patients with Intracranial Tumors," *J. Neurooncol.* 33: 117-130, 1997.
Kahl et al., "Synthesis of Tetrakis-Carborane-Carboxylate Esters of 2,4-bis-(α,β-dihydroxyethyl)-Deuteroporphyrin IX," *J. Chem. Soc., Chem. Commun.* 1769-1771, 1990.
Locher, "Biological Effects and Therapeutic Possibilities of Neutrons," *Amer. J. Roentgenol. Radium Ther.* 36: 1-13, 1936.
Matsumura et al., "A New Boronated Porphyrin (STA-BX909) for Neutron Capture Therapy: An in vitro Survival Assay and in vivo Tissue Uptake Study," *Cancer Lett.* 141: 203-209, 1999.
Miura et al., "Preparation of Carboranyl Porphyrins for Boron Neutron Capture Therapy," *Tetrahedron Lett.* 31: 2247-2250, 1990.
Papadopoulou et al., "Synthesis of Novel 2-Nitroimidazole-Tethered Tricyclic Quinolines, Bearing a Second Heteroatom, and Their in vitro Evaluation as Hypoxia-Selective Cytotoxins and Radiosensitizers," *Bioorg. Med. Chem. Lett.* 14: 1523-1525, 2004.
Pignol et al., "Selective Delivery of $^{10}$B to Soft Tissue Sarcoma Using $^{10}$B-L-Borophenylalanine for Boron Neutron Capture Therapy," *Br. J. Radiol.* 71: 320-323, 1998.
Sasai et al., "Fluorinated 2-Nitroimidazole Derivative Hypoxic Cell Radiosensitizers: Radiosensitizing Activities and Pharmacokinetics," *Int. J. Radiat. Oncol. Biol. Phys.* 29: 579-582, 1994.
Scobie et al., "Tumour-Targeted Boranes. 4. Synthesis of Nitroimidazole-Carboranes with Polyether-Isoxazole Links," *J. Org. Chem.* 59: 7008-7013, 1994.
Scobie et al., "Tumour-Targetted Boranes. Part 3. Synthesis of Carbamate-Linked Nitroimidazolyl Carboranes Designed for Boron Neutron Capture Therapy of Cancer," *J. Chem. Soc Perkin Trans.* 1: 2059-2063, 1994.
Soloway et al., "The Chemistry of Neutron Capture Therapy," *Chem. Rev.* 98: 1515-1562, 1998.
Sugie et al., "Reevaluation of the Radiosensitizing Effects of Sanazole and Nimorazole in vitro and in vivo," *J. Radiat. Res.* 46: 453-459, 2005.
Swenson et al., "Synthesis and Evaluation of a Boronated Nitroimidazole for Boron Neutron Capture Therapy," *J. Med. Chem.* 39: 1540-1544, 1996.
Tolpin et al., "Synthesis and chemistry of Mercaptoundecahydro-closo-dodecaborate(2-)" *Inorg. Chem.* 17: 2867-2873, 1978.
Wood et al., "Uptake and Retention of Nitroimidazole-Carboranes Designed for Boron Neutron Capture Therapy in Experimental Murine Tumours: Detection by $^{11}$B Magnetic Resonance Spectroscopy," *Int. J. Radiat Biol.* 70: 587-592, 1996.
Chinese Patent Office Action for CN200780048105.2, issued Jun. 24, 2011.
Supplementary European Search Report for EP 07871243, dated Nov. 23, 2009.
International Search Report and Written Opinion for PCT/US2007/82548, mailed Aug. 7, 2008.
Bormans et al., "Synthesis, radio-LC-MS analysis and biodistribution in mice of $^{99m}$Tc-NIM-BAT," *J. Label. Compd. Radiopharm.* 46: 575-585 (2003).
Dubois et al., "Evaluation of hypoxia in an experimental rat tumour model by [$^{18}$F]Fluoromisonidazole PET and immunohistochemistry," *Br. J. Cancer* 91:1947-1954 (2004).
Foo et al., "Functional Imaging of Intratumoral Hypoxia," *Mol. Imaging Biol.* 6:291-305 (2004).
Hay et al., "Hypoxia-selective antitumor agents. 10. Bis(nitroimidazoles) and related Bis(nitroheterocycles): Development of derivatives with higher rates of metabolic activation under hypoxia and improved aqueous solubility," *J. Med. Chem.* 38:1928-1941 (1995).
Yamamoto et al., "Synthesis and Characterization of Lipophilic 1-[$^{18}$F]Fluoroalkyl-2-nitroimidazoles for Imaging Hypoxia," *Biol. Pharm. Bull.* 22:590-597 (1999).
Extended European Search Report for European Patent Application No. 07871100.9 dated Nov. 9, 2012.
Office Action for Japanese Patent Application No. 2009-531545 dated Nov. 14, 2012 (English Translation Provided).
Chinese Patent Office Action (CN 200780044283.8) dated Apr. 20, 2012.
Office Action for Chinese Patent Application No. 200780044283.8 dated May 18, 2011 (English Translation).
Papadopoulou et al., "Synthesis of a novel nitroimidazole-spermidine derivative as a tumor-targeted hypoxia-selective cytotoxin," Bioorg Med Chem Lett. 14(6):1519-22 (2004).
Office Action in Canadian Patent Application No. 2,665,494 dated Feb. 25, 2014 (6 pages).

\* cited by examiner

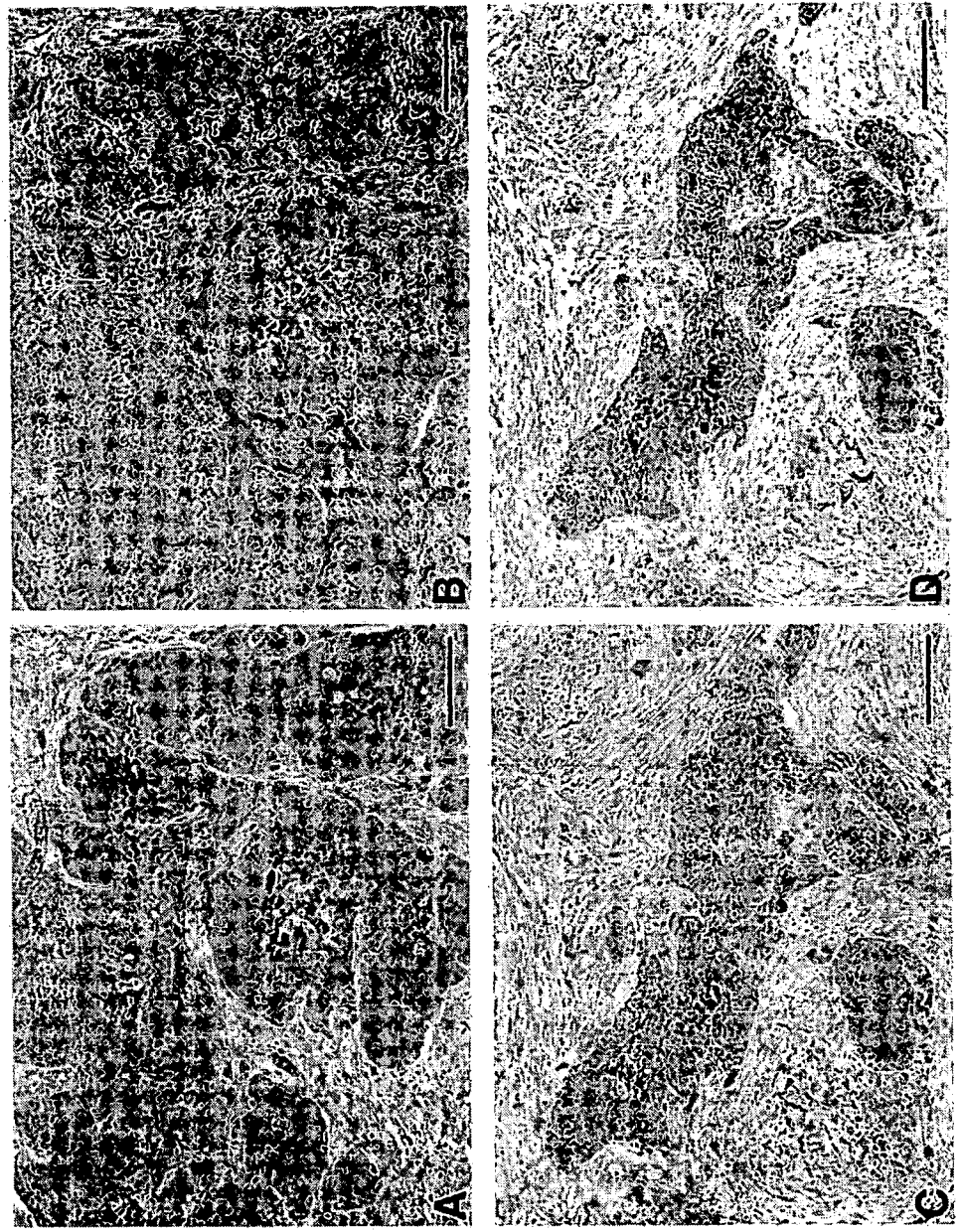

WEAKLY BASIC 2-NITROIMIDAZOLES FOR THE NON-INVASIVE DETECTION OF TISSUE HYPOXIA

FIELD OF THE INVENTION

This invention relates to weakly basic derivatives of 2-nitroimidazoles (pKa about 8 or greater) and their penultimate chemical precursors that are useful for the non-invasive measurement of cellular hypoxia in normal and cancer tissue by means of positron emission tomography (PET), magnetic resonance spectroscopy (MRS), and magnetic resonance imaging (MRI).

BACKGROUND OF THE INVENTION

Hypoxia plays an important role in physiology, pathophysiology and cancer. Recent examples include: hormonal control of tissue oxygenation (Badger et al., Urol Int, 76: 264-268, 2006); bone remodeling (Dodd et al., Am. J. Physiol. Renal. Physiol 277: C598-602, 1999); embryogenesis (Nanka et al., Dev Dyn, 235: 723-733, 2006); teratogenesis (Danielsson et al., Birth Defects Res A Clin Mol Teratol 73: 146-153, 2005); optic nerve ischemia (Danylkova et al., Brain Res 1096: 20-29, 2006); ischemic heart disease (Cheema, et al., J Am Coll Cardiol 47: 1067-1075, 2006); inflammatory disease including arthritis (Peters et al., Arthritis Rheum 50: 291-296, 2004); wound healing (Albina et al., Am J Physiol Cell Physiol 281: C1971-1977, 2001); ischemic kidney disease (Villanueva et al., Am J Physiol Regul Integr Comp Physiol 290: R861-870, 2006); cirrhotic liver disease (Jeong et al., Liver Int 24: 658-668, 2004); lung disease (Morani et al., Proc Natl Acad Sci USA 103: 7165-7169, 2006); alcohol induced pancreatic disease (McKim et al., Arch Biochem Biophys 417: 34-43, 2003); thymic disease (Hale et al., Am J Physiol Heart Circ Physiol 282: H1467-1477, 2002); obstructive disease of urogenital organs (Damaser et al., J Appl Physiol 98: 1884-1890, 2005; Ghafar et al., J Urol 167: 1508-1512, 2002); and, in cancer prognoses (Carnell et al., Int J Radiat Oncol Biol Phys 65: 91-99, 2006; Kaanders et al., Cancer Res 62: 7066-7074, 2002).

Two categories of hypoxia are currently recognized in solid tissues: diffusion-limited chronic hypoxia and perfusion-limited acute or fluctuating hypoxia. In addition to their impact on local radiation control in tumors, acute and chronic hypoxia are believed to contribute to an overall poor prognosis for cancer patients by inducing hypoxia-induced angiogenesis, migration, and invasion factors that increase overall tumor aggressiveness independent of treatment protocol (Vaupel et al., Semin. Oncol. 28:29-35, 2001). Chronic hypoxia is a natural feature of normal tissues such as liver and kidney and is not a pathophysiological condition. However, uncontrolled fluctuations in hypoxia contribute to hypoxia-reperfusion injury by creating reactive oxygen species in normal tissue (Thurman et al., J. Gastroenterol. Hepatol. 13(Suppl):S39-50, 1998).

Chronic hypoxia arises at the distal end of oxygen gradients created by oxygen consumption in cells close to blood vessels compounded, in the case of tumors, by deficiencies in local oxygen supply arising from longitudinal gradients of $pO_2$ in tumor vascular trees (Dewhirst et al., Int. J. Radiat. Oncol. Biol. Phys. 42:723-726, 1998). Thomlinson and Gray first deduced that regions of chronic hypoxia exist in human tumors and proposed that these regions contribute to tumor radiation resistance (Thomlinson and Gray, Br. J. Cancer 9:539-549, 1955).

Acute hypoxia, in contrast to chronic hypoxia with static, metabolically controlled $pO_2$ gradients, is associated with fluctuating $pO_2$ that results from blood flow instabilities which, in the case of tumors, is created by transient vascular occlusion (Dewhirst et al., supra). It has been proposed that acutely hypoxic tumor cells, being proliferative, might be more therapeutically relevant (Wouters et al., Radiat. Res. 147:541-550, 1997) than quiescent, chronically hypoxic cells (Kennedy et al., supra; Varia et al., Gynecol. Oncol. 71:270-277, 1998). In normal tissues, fluctuating hypoxia is associated with hypoxia-reperfusion injury such as alcohol-induced liver disease (Arteel et al., Am. J. Physiol. 271:G494-500, 1996); alcohol-induced pancreatitis (McKim et al., Arch. Biochem. Biophys. 417:34-43, 2003); and, chemotherapy-induced kidney disease (Zhong et al., Am. J. Physiol. 275: F595-604, 1998).

Immunohistochemical hypoxia markers have been used to clearly visualize oxygen gradients in human tumors (Raleigh et al., Br. J. Cancer 56:395-400, 1987; Cline et al., Br. J. Cancer 62:925-931, 1990; Kennedy et al., Int. J. Radiat. Oncol. Biol. Phys. 37:897-905, 1997; and U.S. Pat. No. 5,086,068) and were subsequently used to demonstrate that cellular hypoxia was prognostic for outcome in head and neck cancer (Kaanders et al., Cancer Res. 62:7066-7074, 2002). One of these markers, the HCl salt of the weakly basic 2-nitroimidazole, pimonidazole (1-(2-hydroxy-3-piperidinopropyl)-2-nitroimidazole, pKa=8.7), has been used to measure hypoxia by immunochemical means (U.S. Pat. No. 5,674,693; U.S. Pat. No. 5,086,068). Immunohistochemical analyses are useful for relating cellular hypoxia to other physiological factors such as oxygen-regulated protein expression, vasculature, necrosis, and cellular differentiation, but because they require biopsy tissue, they are invasive, subject to sampling error, unsuitable for routine clinical studies of normal tissue hypoxia, and are less desirable for following changes in human tissue hypoxia because of the inconvenience and discomfort associated with sequential biopsy.

In 1976, Varghese et al. showed that nitroheterocyclic compounds are reductively activated and covalently bound to hypoxic mammalian cells (Varghese et al., Cancer Res. 36:3761-3765, 1976). The addition of the first electron in the cascade of electrons from cellular electron transfer systems that bioreductively activate 2-nitroimidazole hypoxia markers is reversible by molecular oxygen whereby the binding of the markers becomes an indirect measure of tissue hypoxia. In 1981, Chapman et al. demonstrated that the oxygen dependence of binding was in the range of $pO_2$ that rendered tissues resistant to radiation damage (Chapman et al., Br. J. Cancer 43:546-550, 1981). Following the discoveries of Varghese et al. and Chapman et al., attempts were made to translate them into clinically useful techniques for measuring tissue hypoxia. Invasive techniques included autoradiography and scintillation counting of radioactively-labeled 2-nitroimidazoles (Urtasun et al., Br. J. Cancer 54:453-457, 1986); antibody based immunohistochemistry (Raleigh et al., supra; Cline et al., supra; and U.S. Pat. No. 5,086,068); antibody based enzyme linked immunosorbent assay (Raleigh et al., Br. J. Cancer 69:66-71, 1994); and, antibody-based, flow cytometry (Olive et al., Acta. Oncol. 40:917-923, 2001).

Early non-invasive techniques for measuring tissue hypoxia included single photon emission tomography (SPECT; Urtasun et al., Br. J. Cancer Suppl. 27:S209-12, 1996; Iyer et al., Br. J. Cancer 78:163-9, 1998); nuclear medicine (Ballinger et al., J. Nucl. Med. 37:1023-31, 1996; Strauss et al., J. Nucl. Cardiol. 2:437-45, 1995); [19F]magnetic resonance spectroscopy (Raleigh et al., Int. J. Radiat. Oncol. Biol. Phys. 12:1243-5, 1986; Jin et al., Int. J. Radiat. Biol. 58:1025-

34, 1990); and positron emission tomography with 18F-fluoromisonidazole ([18F]FMISO; Rasey et al., Int. J. Radiat. Oncol. Biol. Phys. 17:985-991, 1989). A number of reagents were invented for the purpose of improving upon [18F]fluoromisidazole ([18F]MISO). These included [18F]fluoroetanidazole ([18F]FETA; Rasey et al., J. Nucl. Med. 40:1072-1079, 1999); [18F]fluoroerythronitroimidazole ([18F]FETNIM; Yang et al., Radiology 194:795-800, 1995; Wallace et al., U.S. Pat. No. 5,728,843); [18F]2-(2-nitro-1H-imidazol-1-yl)-N-(3-fluoropropyl)-acetamide([18F]EF1; Evans et al., J. Nucl. Med. 41:327-336, 2000; Koch et al., U.S. Patent Appln. Publn. No. 2005/0026974 A1); [18F]2-(2-nitro-1H-imidazol-1-yl)-N-(2,2,3,3-pentafluoropropyl)-acetamide ([18F]EF5; Ziemer et al., Eur. J. Nucl. Med. Mol. Imaging 30:259-266, 2003; Dobler et al. U.S. Patent Appln. Publn. No. 2006/0159618 A1); [18F]fluoroazomycinarabinofuranoside ([18F] FAZA; Sorger et al., Nucl. Med. Biol. 30:317-326, 2003); 4-bromo-1-(3-[18F]fluoropropyl)-2-nitroimidazole (4-Br-[18F]FPN); and 1-(3-[18F]fluoropropyl)-2-nitroimidazole ([18F]FPN; Yamamoto et al., Biol. Pharm. Bull. 25:616-621). Marginal improvements in tumor to normal tissue ratios, decreased liver uptake, and decreased circulating metabolites were achieved compared to [18F]FMISO.

PET measurement of tissue hypoxia with [18F] labeled 2-nitroimidazoles involves four more or less, independent processes: (1) fixed, rapid radioactive decay of [18F] ($t_{1/2}$=109.8 minutes) attached to hypoxia marker adducts. This constitutes a rapidly decaying hypoxia signal against a dynamic background of (2) wash in and wash out of unmetabolized [18F]hypoxia marker molecules; (3) build up and catabolism of [18F] hypoxia marker protein adducts; and, (4) build up and wash out of [18F] small molecule metabolites of hypoxia markers that include cysteine and glutathione adducts and hydrolytic fragmentation products of the markers (Raleigh and Liu, Int. J. Radiat. Oncol. Biol. Phys. 10:1337-1340, 1984). Approximately 80% of bioreductively activated 2-nitroimidazole hypoxia markers are fragmented by hydrolysis. Fragmentation produces non-binding [18F] metabolites that make a major contribution to background noise but add nothing to the hypoxia signal. Approximately 20% of bioreductively activated 2-nitroimidazole hypoxia markers produce the hypoxia signal—10% from adducts with proteins and 10% from small, thiol containing compounds like glutathione (Raleigh and Koch, Biochem. Pharmacol. 40:2457-2464, 1990). Except for the absence of signal loss due to radioactive decay, non-invasive [19]MRS and [19F] MRI are subject to the same signal-to-noise considerations as [18]PET.

Mathematical models have been designed to isolate the hypoxia signal (protein and glutathione adducts) from background noise (unbound hypoxia marker and its non-binding metabolites), but kinetic data for the concurrent dynamic processes associated with hypoxia marker metabolism are essentially impossible to obtain on a patient-by-patient basis and PET investigators have adopted a simpler concept of fractional hypoxic tumor volume which is the proportion of tumor area (pixels) that possess a tumor-to-blood radioactivity ratio ≥1.4 at a fixed time of 2-3 hours post injection (Koh et al., Int. J. Radiat. Oncol. Biol. Phys. 33:391-398, 1995; Couturier et al., Eur. J. Nucl. Med. Mol. Imaging 31:1182-1206, 2004).

Early studies with 2-nitroimidazole compounds such as [18F]F-MISO (Rasey et al., Int. J. Radiat. Oncol. Biol. Phys. 17:985-991, 1989) and [19F]CCI-103F (Raleigh et al., Int. J. Radiat. Oncol. Biol. Phys. 12:1243-5, 1986) established the potential of [18F]PET and [19]MRS for measuring tissue hypoxia non-invasively, but there remains a need for reagents that improve sensitivity and specificity by improving signal-to-noise limitations for both chronic and acute hypoxia.

SUMMARY OF THE INVENTION

The invention relates to certain novel compounds that are useful as tissue hypoxia detecting agents using positron emission tomography (PET; such as [18F] PET), magnetic resonance spectroscopy (MRS; such as [19F] MRS), and magnetic resonance imaging (MRI; such as [19F] MRI). The novel compounds include penultimate chemical precursors to fluorinated reagents and the [19F] and [18F] fluorinated reagents themselves all of which may be readily synthesized.

A first aspect of the invention features a compound having the structure of formula I

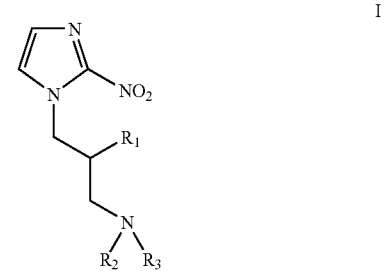

in which R1 is a halogen (e.g., fluorine (F), chlorine (Cl), bromine (Br), iodine (I), or astatine (At)), positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]), non-metal, lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a lower alkyl or a hydroxyalkyl, or are linked to form a five-, six-, or seven-membered heterocyclic ring containing at least one nitrogen atom (e.g., at least 2, 3, or 4 nitrogen atoms); with the caveat that if R1 is hydrogen or hydroxyl, at least one of R2, R3, or the heterocyclic ring contains a halogen, positron emitting radionuclide, non-metal, lower alkyl substituted to contain a halogen, lower alkyl substituted to contain a positron emitting radionuclide, lower alkyl substituted to contain a non-metal, tosylate, mesylate, or tryflate.

In a preferred embodiment of the first aspect of the invention, the compound has the structure of formula III-VI or VIII-XVIII.

A second aspect of the invention features a compound having the structure of formula II

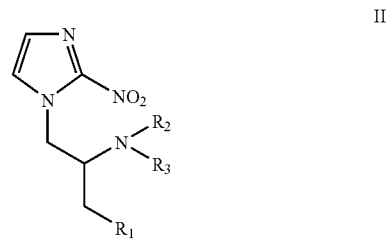

in which R1 is a halogen (e.g., fluorine (F), chlorine (Cl), bromine (Br), iodine (I), or astatine (At)), positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]), non-metal, lower alkyl substituted to contain a halogen, lower alkyl substituted to contain a positron emitting radionuclide, lower alkyl substituted to contain a non-metal, tosylate, mesylate, tryflate, hydrogen, or hydroxyl; and R2 and R3 are independently selected from a lower alkyl or a hydroxyalkyl, or are linked to form a five-, six-, or seven-membered heterocyclic ring containing at least one nitrogen atom (e.g., at least 2, 3, or 4 nitrogen atoms); with the caveat that if R1 is hydrogen or hydroxyl, at least one of R2, R3, or the heterocylic ring contains a halogen, positron emitting radionuclide, non-metal, lower alkyl substituted to contain a halogen, lower alkyl substituted to contain a positron emitting radionuclide, lower alkyl substituted to contain a non-metal, tosylate, mesylate, or tryflate.

In a preferred embodiment of the second aspect of the invention, the compound has the structure of formula VII.

In several embodiments of the first and second aspects of the invention, R2 and R3 are linked to form the five-, six-, or seven-membered heterocycyclic ring; R1 is tosylate, mesylate, or tryflate and R2 and R3 are linked to form the five-, six-, or seven-membered heterocycyclic ring; R2 and R3 are linked to form the five-, six-, or seven-membered heterocycyclic ring and the heterocyclic ring contains 2, 3, or 4 nitrogen atoms, in which at least one of the nitrogen atoms or a carbon atom of the heterocyclic ring is covalently bonded to a lower alkyl or a hydroxyalkyl; R1 is hydroxyl and R2 and R3 are linked to form the five-, six-, or seven-membered heterocycyclic ring, in which at least one carbon or nitrogen atom of the heterocyclic ring is substituted with a haloalkyl (e.g., a fluoroalkyl, such as [19F] or [18F]); R1 is tosylate, mesylate or tryflate and R2 and R3 are independently selected from the group consisting of methyl, ethyl, normal propyl, isopropyl, normal butyl, isobutyl, hydroxymethyl, hydroxyethyl, hydroxypropyl and hydroxybutyl; or R1, R2, R3, or the heterocyclic ring contains a halogen, positron emitting radionuclide, non-metal, lower alkyl substituted to contain a halogen, lower alkyl substituted to contain a positron emitting radionuclide, or lower alkyl substituted to contain a non-metal.

In preferred embodiments of the first and second aspects of the invention, the positron emitting radionuclide is [18F], [79Br], or [124I].

A third aspect of the invention features a method of producing a positron emitting radionuclide-containing compound by (a) providing a compound having the structure of formula I or II:

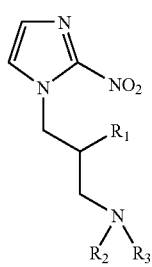

I

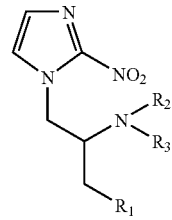

II in which R1 is a tosylate, mesylate, tryflate; and R2 and R3 are independently selected from a lower alkyl or a hydroxyalkyl, or are linked to form a five-, six-, or seven-membered heterocyclic ring containing at least one nitrogen atom (e.g., at least 2, 3, or 4 nitrogen atoms); and (b) reacting the compound with a positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]) in free or salt form under conditions that cause formation of the positron emitting radionuclide-containing compound.

In several embodiments of the third aspect of the invention, R2 and R3 are independently selected from the group consisting of methyl, ethyl, normal propyl, isopropyl, normal butyl, isobutyl, hydroxymethyl, hydroxyethyl, hydroxypropyl and hydroxybutyl; the positron emitting radionuclide is [18F], [79Br], or [124I]; or R2 and R3 are linked to form the five-, six-, or seven-membered heterocyclic ring and the heterocyclic ring contains 2, 3, or 4 nitrogen atoms, in which at least one of the nitrogen atoms or a carbon atom of the heterocyclic ring is covalently bonded to a haloalkyl (e.g, a fluoroalkyl, such as [19F] or [18F]).

A fourth aspect of the invention features a method for detecting hypoxic cells in normal, diseased normal, or malignant tissue (including, e.g., tissues of the brain, lungs, heart, eyes, kidney, liver, pancreas, thymus, intestines, urogenital organs, stomach, and bone, and further including ischemic tissue (e.g., tissue damaged by stroke), inflammatory tissue (e.g., arthritic tissue), tissue undergoing wound healing, and tumor tissue) in a mammal (e.g., a human) by administering to the mammal the compound of the first or second aspect of the invention, in which the compound contains a positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]) or a lower alkyl substituted to contain a positron emitting radionuclide, and detecting any of the compound retained in said normal, diseased normal, or malignant tissue by non-invasive positron emission tomography (PET).

In a preferred embodiment of the fourth aspect of the invention, the positron emitting radionuclide is [18F].

A fifth aspect of the invention features a method for detecting hypoxic cells in normal, diseased normal, or malignant tissue (including, e.g., tissues of the brain, lungs, heart, eyes, kidney, liver, pancreas, thymus, intestines, urogenital organs, stomach, and bone, and further including ischemic tissue (e.g., tissue damaged by stroke), inflammatory tissue (e.g., arthritic tissue), tissue undergoing wound healing, and tumor tissue) in a mammal (e.g., a human) by (a) administering to the mammal a compound having the structure of formula I or II

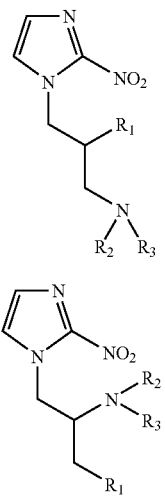

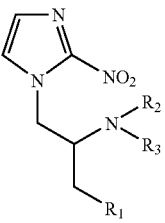

in which R1 is a halogen (e.g., [19F]), lower alkyl substituted to contain a halogen, non-metal (e.g., [31P] or [13C]), lower alkyl substituted to contain a non-metal, tosylate, mesylate, tryflate, hydrogen (e.g., deuterium), or hydroxyl; and R2 and R3 are independently selected from a lower alkyl or a hydroxyalkyl, or are linked to form a five-, six-, or seven-membered heterocyclic ring containing at least one nitrogen atom; with the caveat that if R1 is hydrogen or hydroxyl, at least one of R2, R3, or the heterocylic ring contains a halogen, non-metal, lower alkyl substituted to contain a halogen, lower alkyl substituted to contain a non-metal, tosylate, mesylate, or tryflate; and (b) detecting any of the compound retained in the normal, diseased normal, or malignant tissue by non-invasive magnetic resonance spectroscopy (MRS) or magnetic resonance imaging (MRI).

A sixth aspect of the invention features a method for validating positron emission tomography (PET), magnetic resonance spectroscopy (MRS), or magnetic resonance imaging (MRI) analysis of tissue hypoxia by contacting diseased tissue (e.g., tumor tissue) with an antibody (e.g., a polyclonal or a monoclonal antibody, or antisera that includes the antibody) that specifically binds to an adduct that results following reaction of a protein, polypeptide, polysaccharide, or polynucleotide present in a disease cell (e.g., a tumor cell) with a compound of the first or second aspect of the invention, and detecting binding of the antibody to the diseased tissue, in which an increase in the binding of the antibody to diseased tissue relative to the binding of the antibody to normal tissue validates a determination of tissue hypoxia using PET, MRS, and MRI.

In an embodiment of the sixth aspect of the invention, binding of the antibody to disease tissue is detected using immunofluorescence, immunoperoxidase, cytometry, flow cytometry, or enzyme-linked immunosorbent assay (ELISA). In another embodiment, the analysis of tissue hypoxia is performed using [18F]PET, [19F]MRS, or [19F]MRI.

A seventh aspect of the invention features a for producing an antibody by immunizing a mammal (e.g., a rabbit, monkey, goat, or human) with an adduct that results following reaction of a protein, polypeptide, polysaccharide, or polynucleotide present in a diseased cell (e.g., a tumor cell) with a compound of the first or second aspect of the invention, and collecting antisera or antibodies from the mammal.

An eight aspect of the invention features a kit that includes a container having a compound of the first or second aspect of the invention, a container having a monoclonal or polyclonal antibody, or monoclonal or polyclonal antisera that includes the monoclonal or polyclonal antibody, in which the monoclonal or polyclonal antibody specifically binds to an adduct that results upon reaction of the compound with a protein, polypeptide, polysaccharide, or polynucleotide present in a diseased cell (e.g., a tumor cell), and instructions for using the kit to detect hypoxic cells in tissues.

In a preferred embodiment of the eight aspect of the invention, the instructions describe a method for using the kit to detect the adduct by immunofluorescence, immunoperoxidase, cytometric, flow cytometric, or enzyme linked immunosorbent assay (ELISA).

The novel compounds presently disclosed and claimed all possess weakly basic moieties with general structural formulae I or II.

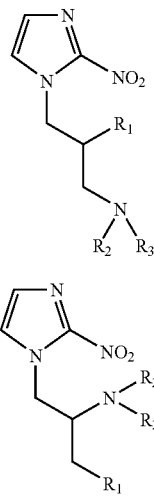

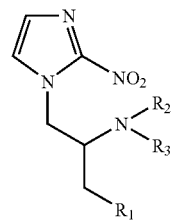

where R1 is independently selected from the group consisting of hydrogen, hydroxyl, tosylate mesylate, tryflate, [19F]fluorine or [18F]fluorine and from a group of lower alkyl mioeties or five-, six-, and seven membered rings containing one or more N atoms. Whereas R2 and R3 are independently selected from a group of lower alkyl, allyl or alkyl mioeties or five-, six-, and seven membered rings containing one or more N atoms wherein R2 and R3 are linked to form five-, six- or seven membered heterocycyclic rings with one or more N atoms. At least one N atom in structure I will be in salt form with anionic counterions that include, but are not limited to, halide. In the case of multiple N atoms in R2 and R3, at least one N may be substituted with a lower alky group. Further, R2 and R3 may be substituted at carbon with a moiety independently drawn from the group of hydrogen, tosylate, mesylate, tryflate, [19F]fluorine or [18F]fluorine.

The invention involves a deliberate and explicit choice of compounds that contain at least one weakly basic moiety that confers pharmacokinetic and pharmacodynamic properties that represent specific improvements over existing reagents for the non-invasive PET, MRS, and MRI analysis of tissue hypoxia.

The invention is intended to improve the use of PET, MRS, and MRI to measure hypoxia in diseased normal and malignant tissue. This includes measuring initial levels of chronic and acute hypoxia with increased sensitivity and following changes in both types of hypoxia in response to therapeutic intervention.

The term "alkyl" as used herein refers to a branched or unbranched saturated hydrocarbon group of 1 to 24 carbon atoms such as methyl, ethyl, normal propyl, isopropyl, normal butyl, isobutyl, tertiary butyl, pentyl, octyl, decyl, eicosyl, tetracosyl and the like. Preferred alkyl groups herein are "lower alkyl groups" containing 1 to 5 carbons.

The term "hydroxyalkyl" refers to alkyl groups containing a hydroxyl group.

The term "tosylate" refers to esters formed when a hydroxyl group reacts with p-toluene sulfonyl chloride, but may include toluene sulfonyl chlorides in which the toluene moiety is substituted with alkyl, halide, ester, ether or cyano groups or the like.

The term "mesylate" refers to esters formed when a hydroxyl group reacts with methane sulfonyl chloride, but may include methane sulfonyl chlorides in which the methane moiety is substituted with alkyl, halide, ester, ether or cyano groups or the like.

The term "triflate" refers to esters formed when a hydroxyl group reacts with trifluoromethane sulfonyl anhydride.

By "within the framework of the ring" is meant the incorporation of an atom or at least one atom of a group within the contiguous atoms of a ring structure.

Examples are presented in terms of fluorinated 2-nitroimidazoles but it is known to those skilled in the art that, in the case of PET, compounds of the invention may be labeled with any positron emitting nuclide, including, e.g., [76Br] and [124I].

It is to be understood that the compounds of the invention may be used for PET, MRS, and MRI detection of tissue hypoxia and that the advantages of reagents that incorporate a weakly basic moiety accrue to [18]PET, [19F]MRS and [19F]MRI. It is also to be understood that the inventors recognize that increasing the number of halogen atoms, such as [19F], by procedures well known to those skilled in the art of chemical synthesis will increase detection sensitivity for MRS/MRI in a manner that increases with the square of the number of halogen atoms present in the compounds.

It is to be understood that intravenous administration is the preferred route for PET studies (using, e.g., [18F]), but that intravenous or oral administration can be used for compounds of the invention, for example, compounds used in [19]MRS or [19F]MRI analyses of tissue hypoxia.

It is to be understood that polyclonal or monoclonal antibodies can be raised against bioreductively produced macromolecular adducts of the compounds of the invention and that these can be used to validate non-invasive PET, MRS and MRI analyses by immunochemical means including immunofluorescence, immunoperoxidase and enzyme linked immunosorbent assays.

Other features and advantages of the invention will be apparent from the following description of the preferred embodiments thereof, and from the claims.

BRIEF DESCRIPTION OF THE DRAWINGS

FIG. 1 is a photomicrograph comparing the immunostaining for the binding of a weakly basic 2-nitroimidazole (left hand panels, A & C) and a 2-nitroimidazole lacking a weakly basic moiety (panels B & D). Panels A & B and panels C & D are from different regions of the same canine adenocarcinoma. Note that in panels C & D, the extent of immunostaining is similar for both hypoxia markers but in panels A & B the extent of binding of the weakly basic marker (panel A) greatly exceeds that for the marker that lacks a weakly basic moiety (panel B) and, furthermore, that the area of more extensive binding in panel A is of lighter intensity than that in panel B. In the presence of strong zones of immunostaining around necrotic regions in the tumors, the light staining is characteristic of acute or fluctuating hypoxia that markers with weakly basic moieties are superior at detecting.

DETAILED DESCRIPTION OF THE INVENTION

The novel compounds and methodologies according to the present invention, which incorporating weakly basic moieties (pKa about 8 or greater) into 2-nitroimidazole hypoxia markers labeled with, e.g., a halogen, a positron-emitting radionuclide, or a non-metal, facilitate the non-invasive analysis of normal tissue hypoxia and the analysis of changes in tissue hypoxia. In particular, the invention provides convenient techniques for measuring hypoxia prior to therapeutic intervention that, in turn, allow for the selection of patients for hypoxia-based therapeutic interventions in an effective and timely manner. The invention also provides a way for following the effectiveness of hypoxia-based, therapeutic interventions in diseased normal and malignant tissue. In particular, the compounds of the invention are useful for detecting hypoxic conditions present in, e.g., tissues of the brain, lungs, heart, eyes, kidney, liver, pancreas, thymus, intestines, urogenital organs, stomach, and bone. The hypoxic conditions can result from ischemia (e.g., as a result of stroke), inflammation, wound healing, and cancer.

The invention provides compounds for the non-invasive detection of both chronic and acute hypoxia using PET, MRS, and MRI. The compounds efficiently detect chronic and acute hypoxia. The compounds of the invention provide increased signal-to-noise ratios and have the ability to detect acute or fluctuating hypoxia with greater sensitivity than prior art markers. The ability to detect acute hypoxia is important because it is widely believed among cancer biologists that acute hypoxia has an inordinate impact on cancer therapy.

Compounds of the invention include fluorinated 2-nitroimidazole derivatives for the non-invasive detection of hypoxia in diseased normal and malignant tissue by means of [18F]PET, [19F]MRS, or [19F]MRI. The 2-nitroimidazole moiety of the compounds undergoes bioreduction to intermediates that bind covalently to peptides and proteins in tissue cells that have a $pO_2 \leq 10$ mmHg, such that stable adducts are formed that act as markers for tissue hypoxia. The introduction of [18F] (and/or other positron emitting radionuclides) or [19F] (and/or other non-radioactive halogens or non-metals) into the 2-nitroimidazole allows for the detection of tissue hypoxia by means of physically non-invasive [18F]PET, [19F]MRS, or [19F]MRI. The compounds of the invention can be used in the non-invasive study of hypoxia in diseased normal tissue (e.g., arthritic tissue) and malignant tissue (e.g., cancer tissue).

The invention can be used in two ways. First, the level of tissue hypoxia prior to therapy can be assessed allowing for selection of patients who may benefit from a hypoxia-based intervention. Second, changes in tissue hypoxia in response to therapeutic interventions, such as ionizing radiation, hyperthermia, hypoxic cell radiosensitizers, bioreductive cytotoxins, anti-inflammatory agents, or growth factor inhibitors can be followed as a measure of the success of the intervention.

The compounds of the invention constitute an improvement over prior art compounds in several respects, not the least of which include the following. 1) The compounds of the invention reduce background "noise" typically observed with existing PET, MRS, and MRI reagents when used in the non-invasive measurement of hypoxia. 2) Acid salts of 2-nitroimidazole compounds possessing a weakly basic substituent are water-soluble, thereby facilitating administration in both human and experimental animal applications. 3) Weakly basic reagents have much shorter plasma half-lives in humans. For example, pimonidazole has a much shorter plasma half-life ($t_{1/2}$=5.1±0.8 hours) than hypoxia markers such as misonidazole ($t_{1/2}$=9.3 hours) or EF5 ($t_{1/2}$=11.7±2.7 hours). Therefore, unmetabolized, weakly basic markers will be cleared much more rapidly from circulation thereby increasing signal-to-noise in, e.g., [18F]PET, [19F]MRS, and [19F]MRI] analyses. 4) Selective uptake of weakly basic PET reagents into tissue cells above extracellular concentrations will increase the rate of binding to hypoxic cells and enhance sensitivity of detection. The methodology of the present invention recognizes that enhanced uptake is the result of differentials between intracellular and extracellular pH in cells of solid tumors. 5) Conjugate bases of compounds of the invention possessing weakly basic substituents (e.g., [18F] PET, [19F]MRS, and [19F]MRI reagents of the invention) have intermediate octanol-water partition coefficients. This means that the compounds readily penetrate all tissues including brain where they are concentrated about 3 fold above plasma levels. Therefore, weakly basic PET, MRS, and MRI compounds of the invention can be used for investigating hypoxia in all normal and tumor tissues, whereas hydrophilic markers in the prior art are effectively excluded from many normal tissues of interest. It is known that central nervous system toxicity is limiting for weakly basic 2-nitroimidazole hypoxia markers. However, PET compounds are used in trace amounts and central nervous system toxicity is not a significant issue. Even relatively high doses (0.5 g/m2; 750-1000 mg/patient; 50% of the maximally tolerated single dose) of the weakly basic hypoxia marker, pimonidazole, has been used clinically with an extremely low frequency of even the mildest of central nervous system (CNS) effects, such as a sensation of warmth, indicating that CNS toxicity would not prevent the use of higher concentrations of the weakly basic 2-nitroimidazole compounds of the present invention for MRS or MRI (e.g., the use of [19F]-fluorinated, weakly basic 2-nitroimidazole compound of the present invention for [19F] MRS or [19F]MRI). 6) Adducts of hypoxia markers with weakly basic substituents are more stable than hypoxia markers that lack a weakly basic substituent. This has the effect of stabilizing the hypoxia signal over currently available PET, MRS, and MRI markers of the prior art (in particular, the fluorinated hypoxia markers of the present invention demonstrate a hypoxia signal that is more stable than the [18F]PET, [19F]MRS, and [19F]MRI hypoxia markers of the prior art). 7) The weakly basic compounds of the present invention permit detection of acute hypoxia with much higher sensitivity than PET, MRS, and MRS markers of the prior art. The weakly basic substituent of the compounds of the invention promotes their concentration in cells experiencing fluctuating hypoxia in a high extracellular pH (pHe) tissue microenvironment. This occurs due to differentials in intracellular and extracellular pH of cells experiencing fluctuating hypoxia; pH gradients exist in solid tissues such that cells experiencing fluctuating hypoxia are at relatively high pH.

Compounds of the Invention

The novel compounds provided herein are those defined by the structural formulas (I) and (II).

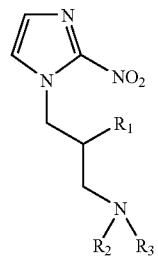

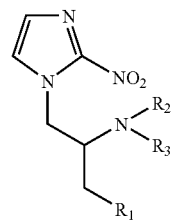

R1 can be selected from a halogen (e.g., fluorine (F), chlorine (Cl), bromine (Br), iodine (I), or astatine (At)), a positron emitting radionuclide (e.g., [11C], [13N], [15O], [18F], [52Fe], [55Co], [61Cu], [62Cu], [64Cu], [62Zn], [63Zn], [70As], [71As], [74As], [76Br], [79Br], [82Rb], [86Y], [89Zr], [110In], [120I], [124I], [122Xe], [94mTc], [94Tc], or [99mTc]), a non-metal, a lower alkyl substituted to contain a halogen, a lower alkyl substituted to contain a positron emitting radionuclide, a lower alkyl substituted to contain a non-metal, a tosylate, a mesylate, a triflate, a hydrogen, or a hydroxyl; and R2 and R3 can be independently selected from a lower alkyl or a hydroxyalkyl, or are linked to form a five-, six-, or seven-membered heterocyclic ring containing at least one nitrogen atom (e.g., at least 2, 3, or 4 nitrogen atoms); with the caveat that if R1 is hydrogen or hydroxyl, at least one of R2, R3, or the heterocylic ring contains a halogen, a positron emitting radionuclide, a non-metal, a lower alkyl substituted to contain a halogen, a lower alkyl substituted to contain a positron emitting radionuclide, a lower alkyl substituted to contain a non-metal, a tosylate, a mesylate, or a triflate.

Preferably, R2 and R3 are linked to form a five-, six-, or seven-membered heterocycyclic ring that has at least one nitrogen atom, but excludes groups in the ring that decrease basicity, such as O, S, or N-acyl. At least one N atom in structure (I) may be in salt form with anionic counterions including, but not limited to, halide. In the case of multiple N atoms, at least one N may be substituted with a lower alkyl, hydroxyalkyl or fluoroalkyl group. Further, R2 and R3 may be substituted at carbon with a moiety independently selected from the group of hydrogen, tosylate, mesylate, triflate, [19F] fluorine or [18F]fluorine.

Examples of preferred compounds within this group are as shown in Chart A:

Chart A
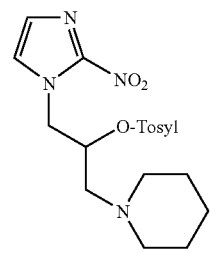 III
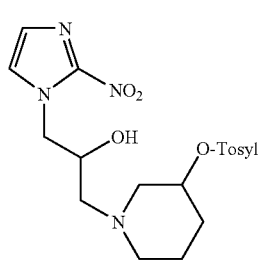 IV
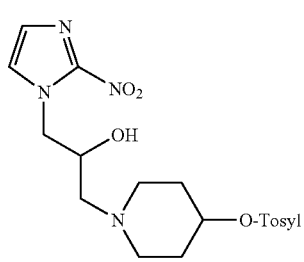 V
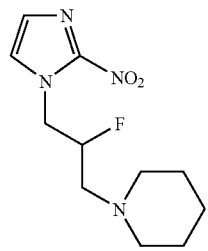 VI
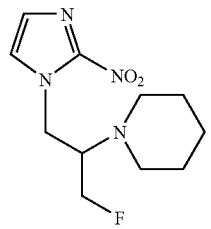 VII
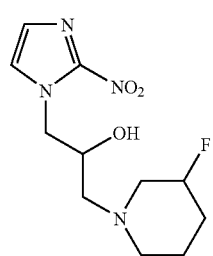 VIII
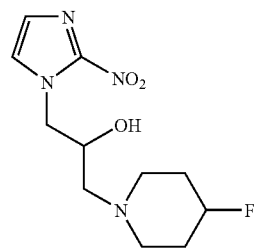 IX
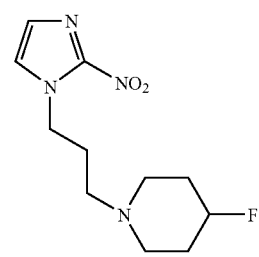 X
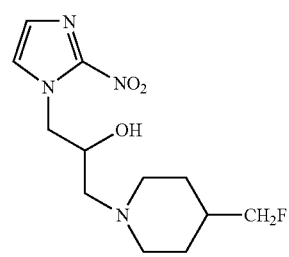 XI
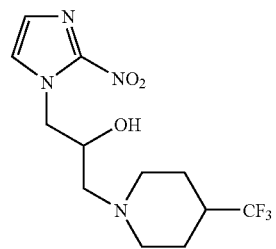 XII
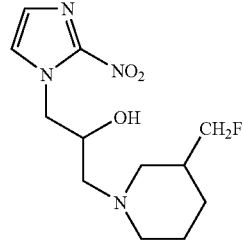 XIII
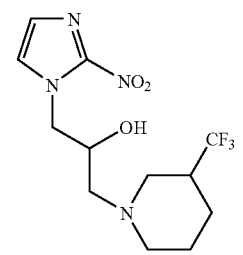 XIV -continued

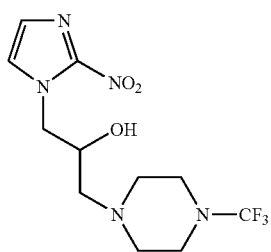

XV

XVI

XVII

XVIII

The compounds defined by structural formulas (VI-XVII), including salts thereof, are useful for detecting hypoxia in diseased normal and malignant tissue either alone or in conjunction with other PET markers of tissue physiology (e.g., [18F]-fluorodeoxyglucose, [18F]-FDG).

Radiolabeled compounds of the invention are useful compositions for imaging, detection, and diagnosis of disease in a subject. Numerous radiolabels may be used to generate radiolabeled compounds that are useful in imaging and detection. For example, a non-limiting list of radiolabels that may be used to generate radiolabeled compounds include 11C, 13N, 15O, 18F, 52Fe, 62Cu, 64Cu, 67Cu, 67Ga, 68Ga, 76Br, 86Y, 89Zr, 94mTc, 94Tc, 99mTc, 111In, 123I, 124I, 125I, 131I, 154-158Gd, and 175Lu. Particularly preferred radiolabels comprise, or alternatively consist of, 18F, 64Cu, 76Br, I124 and mixtures thereof.

As an example, 18F can be obtained from cyclotrons after bombardment of 18O-enriched water with protons. The enriched water containing H-18F can be neutralized with a base having a counter-cation that is any alkylammonium, tetraalkylammonium, alkylphophosphonium, alkylquanidium, alkylamidinium, or alkali metal (M), such as potassium, cesium, or other monovalent ions that are strongly chelated to a ligand such as Kryptofix 222 (4,7,13,16,21,24-hexaoxa-1,10-diazabycyclo[8.8.8]hexacosane), such that the resulting alkali metal-ligand complex is freely soluble in organic solvents such as acetonitrile, dimethylsulfoxide, or dimethylformamide. The water can be evaporated off to produce a residue of countercation-18F, which can be taken up in an organic solvent for further use. In general, the counter-cation is selected to enable the fluoride ion to react rapidly in an organic phase with a halogen.

Because fluoride is the most electronegative element, it has a tendency to become hydrated and lose its nucleophilic character. To minimize this, the labeling reaction preferably is performed under anhydrous conditions. For example, fluoride (as potassium fluoride or as a complex with any of the other counter-ions discussed above) can be placed in organic solvents, such as acetonitrile or THF. With the assistance of agents that bind to the counter-cation, such as Kryptofix 2.2.2 (4,7,13,16,21,24-hexaoxa-1,10-diazabicyclo[8.8.8]-hexacosane), the fluoride ion becomes very nucleophilic in these solvents. The remaining portion of the chelate molecule of the invention then can be added to the solvent and the chelate thereby labeled with the 18F.

Although potassium is useful as the metal in the counter-cations in accordance with the present invention, cesium may be preferred to potassium because cesium is a larger ion with a more diffuse charge. Accordingly, cesium has looser ionic interactions with the small fluoride atom, and therefore does not interfere with the nucleophilic properties of the fluoride ion. For similar reasons, potassium may be preferred to sodium, and, in general, the suitability of a lanthanide metal as the metal in the counter-cation in accordance with the present invention increases as you go down the periodic table. Group Ib reagents, such as silver, also are useful as counter-ions in accordance with the present invention. Further, organic phase transfer-type ions, such as tetraalkylammonium salts, also can be used as counter-cations.

Formulations of the Compounds of the Invention

The compounds of the invention can be used to preferentially target tumor tissue. Compounds of the invention may be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18th edition), ed. A. Gennaro, 1990, Mack Publishing Company, Easton, Pa. Pharmaceutical formulations of a therapeutically effective amount of a compound of the invention, or pharmaceutically acceptable salt-thereof, can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration.

Methods well known in the art for making formulations are found, for example, in *Remington's Pharmaceutical Sciences* (18th edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the peptide agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the chemical compound being administered, the time of administration, the route of administration, the nature of the formulation, the rate of excretion, the nature of the subject's conditions, and the age, weight, health, and gender of the patient. In addition, the severity of the condition targeted by a compound of the invention will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The compounds of the invention may be prepared in high yield using simple straightforward methods as exemplified by the examples below. It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

The following examples are provided so that those of ordinary skill in the art can see how to make and use the compounds of the invention. The examples are not intended to limit the scope of what the inventors regard as their invention. All starting materials and reagents are commercially available.

EXAMPLES

Example 1

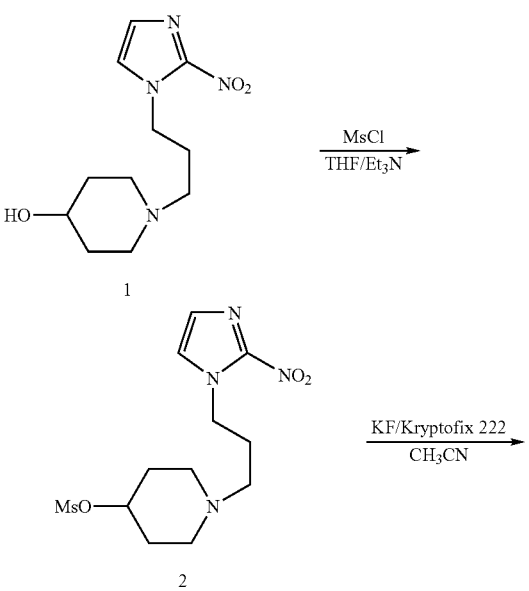

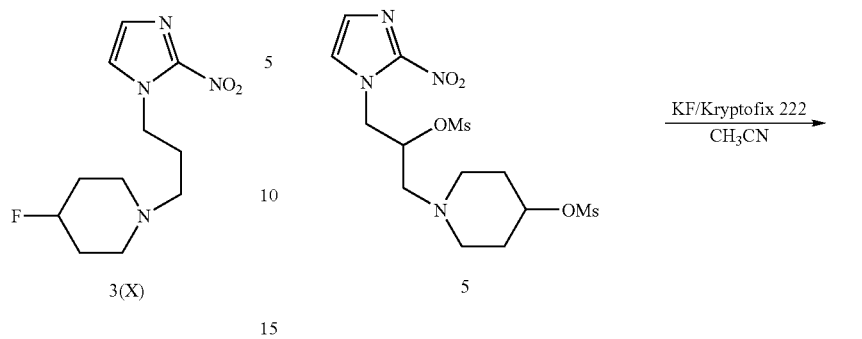

The starting material (1) (460 mg, 1.8 mmol) was dissolved in 50 ml THF and Et$_3$N (0.5 ml) was added and followed by dropwise addition of MsCl (0.28 ml, 3.6 mmol). The reaction was stirred at room temperature for 20 min. Thin layer chromatography (TLC) showed the starting material was almost completely reacted. After the workup the crude reaction product was purified by column chromatograph (EtOAc) to afford 500 mg of desired mesylated product (2) (yield is 84%). $^1$HNMR(DMSO-d$_6$, δppm): 1.63 (m, 2H, CH$_2$), 1.90 (m, 4H, 2×CH$_2$), 2.10 (m, 2H, CH$_2$), 2.24 (t, 2H, CH$_2$, J=6.9 Hz), 2.48 (m, 2H, CH$_2$), 3.15 (s, 3H, CH$_3$), 4.41 (t, 2H, CH$_2$, J=6.9 Hz), 4.60 (m, 1H, CH), 7.15 (d, 1H, CH=, J=1.2 Hz), 7.65 (d, 1H, CH=, J=1.2 Hz).

Kryptofix 222 (270 mg, 0.72 mmol) was dissolved in 5 ml of acetonitrile (CH$_3$CN). To this solution was added anhydrous powder potassium fluoride (99.99+%, 33 mg, 0.57 mmol) followed by mesylate (2) (80 mg, 0.24 mmol). The resulting mixture was refluxed for 2 hrs in an oil bath (95-100° C.). After workup, the crude reaction product was purified by preparative TLC to give 31 mg of fluoride (3, X). The overall yield was 50%. For Compound (3,X): $^1$HNMR (DMSO-d$_6$, δppm): 1.67 (m, 2H, CH$_2$), 1.92 (m, 4H, 2×CH$_2$), 2.07 (m, 2H, CH$_2$), 2.23 (t, 2H, CH$_2$, J=6.6 Hz), 2.53 (m, 2H, CH$_2$), 4.13 (brs, 1H, CH), 4.41 (t, 2H, CH$_2$, J=6.9 Hz), 7.15 (s, 1H, imidazole), 7.64 (s, 1H, imidazole). $^{13}$C NMR (DMSO-d$_6$, δ$_{ppm}$): 27.34, 35.87, 48.32, 51.40, 54.83, 58.84, 128.41, and 128.58.

Example 2

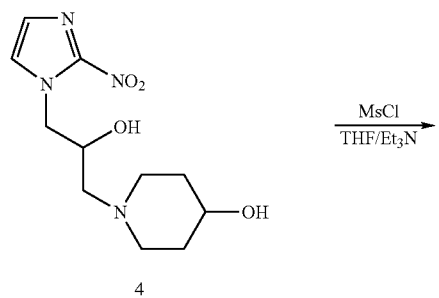

The starting material (4) (4 g, 14.85 mmol) was dissolved in 200 ml THF. To this solution was added Et$_3$N (5 ml) followed by dropwise addition of MsCl (3 ml, 38.8 mmol). The reaction was stirred at room temperature for 30 min. TLC showed that the starting material was almost all consumed. After the workup, the crude reaction mixture was purified by flash column chromatograph (EtOAc) to afford 3.1 g of di-mesylated product (5), yield is 49.1%. $^1$HNMR(DMSO-d$_6$, δppm): 1.71 (m, 2H, CH$_2$), 1.93 (m, 2H, CH$_2$), 2.47 (m, 2H, CH$_2$), 2.68 (m, 4H, 2× CH$_2$), 3.05 (s, 3H, CH$_3$SO—), 3.16 (s, 3H, CH$_3$SO—), 4.55 (dd, 1H, imidazole-CH$_a$—, J=14.4 Hz, 8.7 Hz), 4.66 (m, 1H, O—CH), 4.84 (dd, 1H, imidazole-CH$_a$—, J=14.4 Hz, 8.7 Hz), 5.00 (m, 1H, O—CH), 7.16 (d, 1H, imidazole, J=0.9 Hz), 7.59 (d, 1H, imidazole, J=0.9 Hz).

Kryptofix 222 (MW 376.5, 42 mg, 0.112 mmol) was dissolved in 2 ml of acetonitrile (CH$_3$CN). To this solution was added anhydrous potassium fluoride (99.99+%, 22 mg, 0.379 mmol) followed by di-mesylate (5) (28 mg, 0.0658 mmol). After the di-mesylate (5) was all dissolved, the mixture was refluxed for 30 min. After the workup, the crude reaction mixture was purified by preparative TLC to give 20 mg (87% yield) of mono-fluorine exchanged compound (6). For compound (6): $^1$HNMR(DMSO-d$_6$, δppm): 1.68 (m, 2H, CH$_2$), 1.90 (m, 2H, CH$_2$), 2.43 (m, 2H, CH$_2$), 2.62 (m, 2H, CH$_2$), 2.74-2.89 (m, 2H, piperidine-CH$_2$), 3.11 (s, 3H, CH$_3$SO—), 4.36-4.51 (m, 1H, imidazole-CH), 4.68-4.90 (m, 2H, imidazole-CH, F—H), 5.06 (m, 1H, O—CH), 7.12 (d, 1H, imidazole, J=0.9 Hz), 7.19 (d, 1H, imidazole, J=0.9 Hz). $^{13}$C NMR (DMSO-d$_6$, δppm): 25.89, 32.06, 50.21 (d, J$_{F—C}$=20.44 Hz), 55.32, 60.15 (d, J$_{F—C}$=20.81 Hz), 65.89, 89.63 (d, J$_{F—C}$=169.68 Hz), 127.55, 128.46.

Example 3

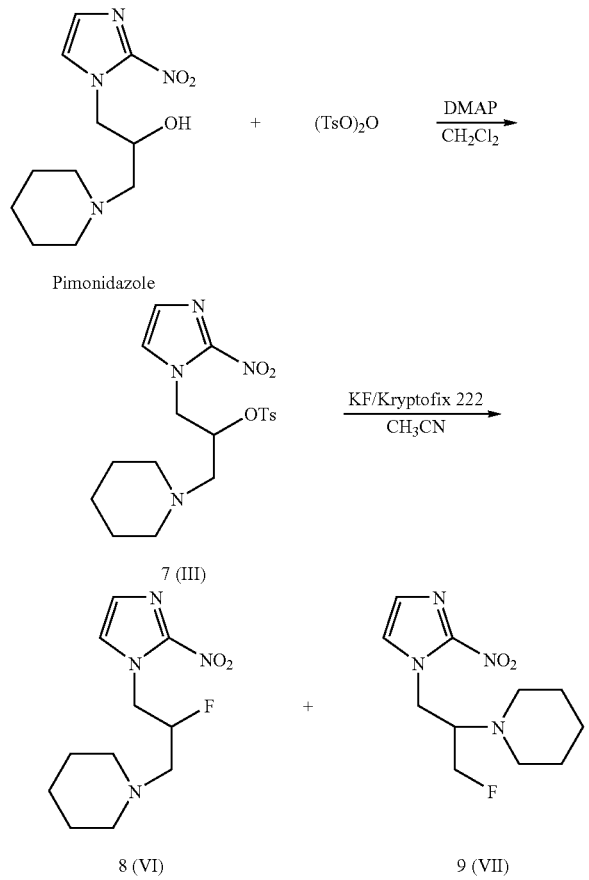

Pimonidazole (3.7 g, 14.5 mmol), p-toluenesulfonic anhydride (5.7 g, 17.5 mmol) and DMAP (1.78 g, 14.5 mmol) were added to 100 ml of anhydrous $CH_2Cl_2$ at 0° C. in an ice-water bath. After stirring for 30 min, the reaction was quenched with water and extracted with ethyl acetate. The organic phase was washed with water, dried over anhydrous sodium sulfate, filtered and concentrated. The crude reaction product was purified by column chromatography (EtOAc-Hexane=1:1) to afford 4.1 g (70% yield) of the desired tosylate (7, III). For compound (7, III): $^1$H NMR (CDCl$_3$, $\delta_{ppm}$): 1.41 (m, 2H, CH$_2$), 1.52 (m, 4H, 2×CH$_2$), 2.33-2.67 (m, 6H, 3×CH$_2$), 2.44 (s, 3H, CH$_3$), 4.29 (dd, 1H, imidazole-CH$_a$—, J=14.4 Hz, 8.7 Hz), 4.87 (m, 1H, O—CH—), 4.97 (dd, 1H, imidazole-CH$_b$—, J=14.7 Hz, J=2.7 Hz), 7.03 (d, 2H, Benzene, J=8.4 Hz), 7.25 (d, 1H, imidazole, J=0.6 Hz), 7.26 (d, 1H, imidazole, J=0.6 Hz), 7.54 (d, 2H, Benzene, J=8.4 Hz). $^{13}$C NMR (CDCl$_3$, $\delta_{ppm}$): 21.87, 24.17, 26.10, 52.08, 55.58, 60.04, 77.42, 127.59, 127.67, 128.38, 130.22, 132.38, 145.82.

Kryptofix 222 (MW 376.5, 824 mg, 2.19 mmol) was dissolved in 6 ml of acetonitrile (CH$_3$CN). To this solution was added anhydrous potassium fluoride (99.99+%, 128 mg, 2.19 mmol) followed by tosylate (7, III) (300 mg, 0.73 mmol). After the tosylate was totally dissolved, the reaction mixture was refluxed for 2 hrs in an oil bath at 95° C. After the workup, the crude reaction product was purified by column chromatography (EtOAc-Hexane=1:1) to afford 600 mg (32% yield) of target fluorinated product (8, VI), along with 550 mg (29.4% yield) of by-product (9, VII).

For compound (8, VI), $^1$H NMR (CDCl$_3$, $\delta_{ppm}$): 1.37 (m, 2H, CH$_2$), 1.52 (m, 4H, 2×CH$_2$), 2.39 (m, 4H, 2×CH$_2$), 2.49-2.66 (m, 2H, piperidine-CH$_2$), 4.45-4.58 (m, 1H, imidazole-CH), 4.79-5.02 (m, 2H, imidazole-CH, F—H), 7.10 (d, 1H, imidazole, J=0.9 Hz), 7.15 (d, 1H, imidazole, J=0.9 Hz). $^{13}$C NMR(CDCl$_3$, $\delta_{ppm}$): 23.87, 25.81, 51.81 (d, J$_{F-C}$=21.2 Hz), 55.32, 59.33 (d, J$_{F-C}$=21.8 Hz), 90.14 (d, J$_{F-C}$=174.6 Hz), 126.97, 128.22.

For compound (9, VII), $^1$H NMR (CDCl$_3$, $\delta_{ppm}$): 1.40 (m, 6H, 3×CH$_2$), 2.37 (m, 2H, piperidine ring: —N—H$_a$), 2.68 (m, 2H, piperidine ring: —N—H$_e$), 2.82-3.32 (m, 1H, piperidine-CH), 4.56 (ddd, 1H, F—H$_a$, J$_{F-H}$=89.1 Hz, J$_{H-H}$=10.2 Hz, 3.9 Hz), 4.49 (d, 2H, CH$_2$, J=6.9 Hz), 4.53-4.59 (m, 1H, F—H$_b$), 7.08 (d, 1H, imidazole, J=0.9 Hz), 7.09 (d, 1H, imidazole, J=0.9 Hz). $^{13}$C NMR(CDCl$_3$, $\delta_{ppm}$): 24.27, 26.28, 47.18 (d, J$_{F-C}$=7.4 Hz), 50.86, 64.88 (d, J$_{F-C}$=17.8 Hz), 80.79 (d, J$_{F-C}$=172.5 Hz), 126.93, 127.85.

Example 4

Preparation of 1-(2-hydroxy-3-(N'-1,1,1,3,3,3-hexafluoroisopropylpiperazino)-2-nitroimidazole (XVI)

2-Nitroimidazole (1 molar equivalent) in acetone was mixed with epichlorohydrin (1.1 molar equivalent) and potassium carbonate (0.001 molar equivalent). The mixture was refluxed overnight and taken to dryness in vacuo to give 1-(2-hydroxy-3-chloropropyl)-2-nitroimidazole. 1-(2-Hydroxy-3-chloropropyl)-2-nitroimidazole is taken up in ethyl acetate and mixed with an equal volume of 10% aqueous sodium hydroxide with vigorous stirring for 1 hour at room temperature. The ethyl acetate layer was washed with water, dried over anhydrous sodium sulfate and taken to dryness to give 1-(2,3-epoxypropyl)-2-nitroimidazole. 1-(2,3-epoxypropyl)-2-nitroimidazole (1 molar equivalent) dissolved in acetone was mixed with N'-1,1,1,3,3,3-hexafluoroisopropylpiperazine (1.1 molar equivalent) and the solution refluxed overnight. The reaction solution was taken to dryness in vacuo to give 1-(2-hydroxy-3-(N'-1,1,1,3,3,3-hexafluoroisopropylpiperazino)-2-nitroimidazole (XVI) that was recrystallized from ethanol. The chemical intermediate, N'-1,1,1,3,3,3-hexafluoroisopropylpiperazine, was prepared by heating 1,1,1,3,3,3-hexafluoroisopropyl bromide (1.0 molar equivalent) and piperazine (1.1 molar equivalent) at reflux in ethanol overnight. The chemical intermediate 1,1,1,3,3,3-hexafluoroisopropyl bromide was prepared by reacting commercially available 1,1,1,3,3,3-hexafluoroisopropyl alcohol (1 molar equivalent) with phosphorus tribromide (0.33 molar equivalent) in ethyl ether overnight at room temperature.

Example 5

Weakly basic 2-nitroimidazole hypoxia compounds of the invention are more sensitive detectors of hypoxia in cells at high pH than are 2-nitroimidazoles that lack a weakly basic moiety, such as CCI-103F. pH-dependent binding for weakly basic pimonidazole was compared to that for CCI-103F in Chinese hamster V79-4 lung fibroblasts under conditions of short-term anoxia. The pH range used (6.4 to 7.4) encompasses about 90% of extracellular pHs measured in human tumors. Eagle's minimum essential medium (MEM) containing 4.5 g/L glucose, but no carbonate, was warmed to 37° C. in a warm room and adjusted to pH 6.4, 6.8 and 7.4 by the addition of sodium bicarbonate under a stream of 5% $CO_2$+95% nitrogen. Fetal bovine serum (FBS) was added to produce an Eagle's pH adjusted MEM containing 10% FBS.

Attached V79-4 cells were harvested with EDTA-trypsin and diluted in 25 mL of the pH adjusted MEM at a concentration of $3\times10^5$ cells/mL. To this solution was added an amount of a stock solution of pimonidazole HCl or CCI-103F to produce a final concentration of 200 uM. The cell solution was then incubated under an atmosphere of 5% CO2+95% nitrogen with agitation for 3 hours. Cell lysates were analyzed by ELISA and the data normalized to protein content. The experiments for both markers were performed in triplicate.

The intensity of pimonidazole binding was greater than that for CCI-103F at all pH levels tested with the difference being greatest at the highest pH tested (Table 1). These data indicate that weakly basic 2-nitroimidazole hypoxia markers are superior reagents at all pH's but are particularly advantageous for the detection of hypoxia in microregions of tissues in which cells are at a relatively high pH. This is a direct result of the fact that intracellular concentrations (Ci) of weakly basic 2-nitroimidazoles increase steeply relative to extracellular concentrations (Ce) with increasing pH whereas no such effect is seen with 2-nitroimidazoles that lack a weakly basic moiety. Because regions in tumors include cells that experience fluctuating hypoxia and a relatively high pH microenvironment, the compounds of the invention, which exhibit increased binding to cells at high pH, are superior at detecting fluctuating hypoxia.

TABLE 1 pH dependence of pimonidazole and CCI-103F binding to anoxic V79 cells.

| pH | Pimonidazole binding (ng/g protein ± SE) | CCI-103 binding (ng/g protein ± SE) | Ci/Ce in V79 cells | |
|---|---|---|---|---|
| | | | Pimonidazole* | CCI-103F* |
| 6.4 | 144 ± 15 | 90 ± 7 | 1.0 | ~1.0 |
| 6.8 | 293 ± 19 | 118 ± 17 | 1.6 | ~1.0 |
| 7.4 | 363 ± 22 | 125 ± 5 | 3.3 | ~1.0 |

*After Wardman, Advanced Topics on Radiosensitizers of Hypoxic Cells (Eds. A. Breccia, C. Rimondi and G. E. Adams), Plenum Press, New York, pp. 49-75, 1982.

Example 6

Weakly basic 2-nitroimidazole hypoxia compounds of the invention are more efficient at detecting fluctuating hypoxia than are compounds that lack a weakly basic moiety when measured in large spontaneous canine tumors analogous to those occurring in humans. The hydrochloride salt of the weakly basic hypoxia marker, pimonidazole, was given to 12 dogs at a dosage of 0.5 gm/m$^2$ body surface area. Seven hours later, all 12 dogs received CCI-103F, a marker that lacks a weakly basic moiety. Two to four, widely separated biopsy samples were taken from viable regions in each tumor and immediately placed in cold 10% neutral buffered formalin. The specimens were fixed for 18-24 hours at 4° C. and then transferred into cold 70% ethanol and stored at 4° C. until mounted into paraffin blocks. Sections from formalin-fixed paraffin-embedded biopsy samples were immunostained for pimonidazole and CCI-103F binding using primary rabbit polyclonal antisera to pimonidazole and CCI-103F adducts respectively. Immunostained sections were exhaustively scanned at 400× by means of an Axioskop 50 microscope and Fluar objective and the percent immunostaining for pimonidazole and CCI-103F adducts was measured.

On average, immunostaining for pimonidazole binding was more extensive than that for CCI-103F (factor 1.25 by paired t test (p=0.032)), but, importantly, on a tumor-by-tumor basis, the factor ranged from 1.0 to 1.65. Furthermore, within a single tumor the extent of pimonidazole binding was similar to that for CCI-103F in some regions (FIGS. 1C & 1D) but greatly exceeded it in other regions (FIGS. 1A & 1B) with a notable component of lighter immunostaining closer to blood vessels. Little difference in the binding between 2-nitroimidazole compounds with and without a weakly basic moiety is expected in cells in areas of chronic hypoxia in the center of tumor nests because these regions are at low, unchanging pH (Helmlinger et al., Nature, Medicine 3: 177-182, 1997; compare FIGS. 1C & 1D). In contrast to chronic hypoxia, fluctuating or acute hypoxia close to blood vessels occurs in regions of steeply rising pH (Helmlinger et al., Nature, Medicine 3: 177-182, 1997); the weakly basic compounds of the invention exhibit increased binding to cells in these regions relative to the binding exhibited by hypoxia markers that lack a weakly basic moiety (compare FIGS. 1A & 1B). In general, hypoxia markers lacking a weakly basic moiety will exhibit reduced binding to cells in regions experiencing acute, fluctuating hypoxia, as is present in regions containing tumors, thereby making detection of tumors more difficult. In contrast, acute, fluctuating hypoxic condition are optimal for the binding of the weakly basic hypoxia compounds of the invention, which will, therefore, be more responsive to fluctuating, acute hypoxia than 2-nitroimidazole hypoxia markers that lack a weakly basic moiety.

These data indicate that weakly basic, 2-nitroimidazole compounds labeled with [18F] or [19F] are more effective than prior art hypoxia markers lacking a weakly basic moiety for non-invasively detecting hypoxia in mammalian tissue.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A compound having the structure of formula I or a pharmaceutically acceptable salt thereof:

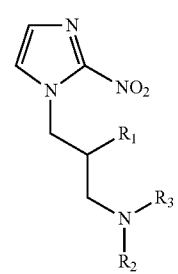

I wherein:
R1 is hydrogen, hydroxyl, tosylate, mesylate, triflate, a positron emitting radionuclide selected from $^{11}C$, $^{13}N$, $^{15}$O, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, a non-metal selected from $^{31}$P and $^{13}$C, a lower alkyl having 1 to 5 carbon atoms that is substituted to contain a halogen, a lower alkyl having 1 to 5 carbon atoms that is substituted to contain a positron emitting radionuclide selected from $^{11}$C, $^{13}$N, $^{15}$O, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, or a lower alkyl having 1 to 5 carbon atoms that is substituted to contain a non-metal selected from $^{31}$P and $^{13}$C; and R2 and R3 are independently selected from a lower alkyl having 1 to 5 carbon atoms and a hydroxyalkyl, or R2 and R3 are linked to form a five-, six-, or seven-membered heterocyclic ring comprising at least one nitrogen atom;

wherein:

i) when R1 is hydrogen, at least one of R2, R3, or said heterocyclic ring comprises a substituent selected from a halogen, a positron emitting radionuclide selected from $^{11}$C, $^{13}$N, $^{15}$O, $^{18}$F, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, a non-metal selected from $^{31}$P and $^{13}$C, a lower alkyl having 1 to 5 carbons that is substituted to contain a halogen, a lower alkyl having 1 to 5 carbon atoms that is substituted to contain a positron emitting radionuclide selected $^{11}$C, $^{13}$N, $^{15}$O, $^{18}$F, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, a lower alkyl having 1 to 5 carbon atoms that is substituted to contain a non-metal selected from $^{31}$P and $^{13}$C, tosylate, mesylate, or triflate; and ii) when R1 is hydroxyl, R2 and R3 are linked to form a five-, six-, or seven-membered heterocyclic ring comprising at least one nitrogen atom, wherein said heterocyclic ring comprises a substituent, wherein said substituent is a halogen, a positron emitting radionuclide selected from any one of $^{11}$C, $^{13}$N, $^{15}$O, $^{18}$F, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, a lower alkyl having 1 to 5 carbon atoms that is substituted to contain a halogen, a lower alkyl having 1 to 5 carbon atoms that is substituted to contain a positron emitting radionuclide selected from any one of $^{11}$C, $^{13}$N, $^{15}$O, $^{18}$Fe, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, a lower alkyl having 1 to 5 carbon atoms that is substituted to contain a non-metal selected from $^{31}$P and $^{13}$C, tosylate, mesylate, or triflate.

2. The compound of claim 1 or a pharmaceutically acceptable salt thereof, wherein R2 and R3 are linked to form said five-, six-, or seven-membered heterocyclic ring.

3. The compound of claim 1 or a pharmaceutically acceptable salt thereof, wherein R2 and R3 are linked to form said five-, six-, or seven-membered heterocyclic ring, and said heterocyclic ring comprises 2, 3, or 4 nitrogen atoms; and wherein at least one of said nitrogen atoms or a carbon atom of said heterocyclic ring is covalently bonded to a lower alkyl or a hydroxyalkyl.

4. The compound of claim 1 or a pharmaceutically acceptable salt thereof, wherein R1 is tosylate, mesylate or triflate and R2 and R3 are linked to form said five-, six-, or seven-membered heterocyclic ring.

5. The compound of claim 1 or a pharmaceutically acceptable salt thereof, wherein R1 is hydroxyl and R2 and R3 are linked to form said five-, six-, or seven-membered heterocyclic ring, wherein at least one carbon or nitrogen atom of said heterocyclic ring is substituted with a haloalkyl.

6. The compound of claim 5 or a pharmaceutically acceptable salt thereof, wherein said haloalkyl is a fluoroalkyl containing $^{19}$F or $^{18}$F.

7. The compound of claim 5 or a pharmaceutically acceptable salt thereof, wherein said heterocyclic ring contains 2, 3, or 4 nitrogen atoms.

8. The compound of claim 1 or a pharmaceutically acceptable salt thereof, wherein R1 is tosylate, mesylate or triflate and R2 and R3 are independently selected from the group consisting of methyl, ethyl, normal propyl, isopropyl, normal butyl, isobutyl, hydroxymethyl, hydroxyethyl, hydroxypropyl and hydroxybutyl.

9. The compound of claim 1 or a pharmaceutically acceptable salt thereof, wherein R1 is tosylate, mesylate, triflate, a positron emitting radionuclide selected from $^{11}$C, $^{13}$N, $^{15}$O, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, and a non-metal selected from $^{31}$P and $^{13}$C, a lower alkyl having 1 to 5 carbon atoms that is substituted to contain a positron emitting radionuclide selected from $^{11}$C, $^{13}$N, $^{15}$O, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, and $^{122}$Xe, or a lower alkyl having 1 to 5 carbon atoms that is substituted to contain a non-metal selected from $^{31}$P and $^{13}$C and R2, R3, or said heterocyclic ring comprises a halogen, a positron emitting radionuclide, a non-metal selected from $^{31}$P and $^{13}$C, a lower alkyl substituted to contain a positron emitting radionuclide, or a lower alkyl substituted to contain a non-metal selected from $^{31}$P and $^{13}$C.

10. The compound of claim 9 or a pharmaceutically acceptable salt thereof, wherein R2, R3, or said heterocyclic ring comprises a halogen.

11. The compound of claim 9 or a pharmaceutically acceptable salt thereof, wherein R2, R3, or said heterocyclic ring comprises a positron emitting radionuclide, wherein said positron emitting radionuclide is $^{11}$C, $^{13}$N, $^{15}$O, $^{18}$F, $^{52}$Fe, $^{55}$Co, $^{61}$Cu, $^{62}$Cu, $^{64}$Cu, $^{62}$Zn, $^{63}$Zn, $^{70}$As, $^{71}$As, $^{74}$As, $^{76}$Br, $^{79}$Br, $^{82}$Rb, $^{86}$Y, $^{89}$Zr, $^{110}$In, $^{120}$I, $^{124}$I, or Xe.

12. The compound of claim 1 or a pharmaceutically acceptable salt thereof, wherein R1 is a positron emitting radionuclide selected from $^{79}$Br and $^{124}$I.

13. The compound of claim 1, wherein said compound has the structure of any one of the following or a pharmaceutically acceptable salt thereof:

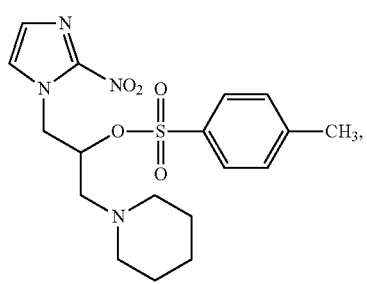

III

-continued
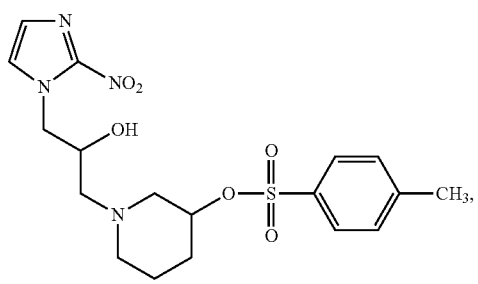
IV
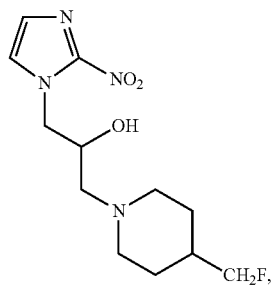
XI
V
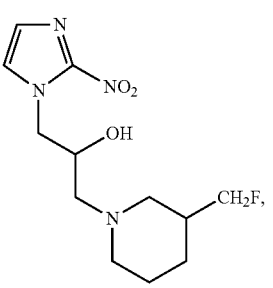
XII
XIII
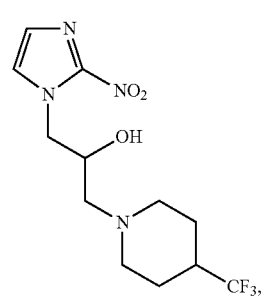
VIII
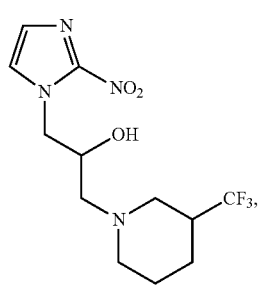
IX
XIV
X
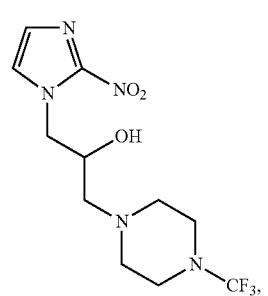
XV

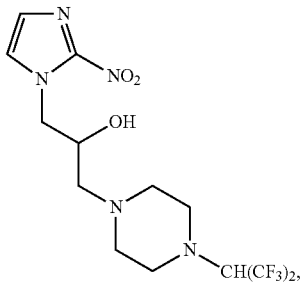

XVI

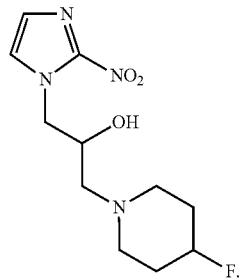

IX

XVII

XVIII

14. A method for detecting hypoxic cells in tissue in a mammal comprising administering to said mammal the compound of claim 1, or a pharmaceutically acceptable salt thereof, wherein said compound comprises said positron emitting radionuclide or said lower alkyl having 1 to 5 atoms that is substituted to contain a positron emitting radionuclide, and detecting any of the compound retained in said tissue by non-invasive positron emission tomography (PET).

15. The method of claim 14, wherein said positron emitting radionuclide is $^{18}F$.

16. A method for detecting hypoxic cells in tissue in a mammal comprising:
 (a) administering to said mammal the compound of claim 1, or a pharmaceutically acceptable salt thereof; and
 (b) detecting any of said compound retained in said tissue by non-invasive magnetic resonance spectroscopy (MRS) or magnetic resonance imaging (MRI).

17. The method of claim 16, wherein said compound comprises $^{19}F$.

18. The method of claim 16, wherein said compound comprises $^{31}P$ or $^{13}C$.

19. The method of claim 16, wherein said compound comprises deuterium.

20. A compound having the following structure or a pharmaceutically acceptable salt thereof:

21. The compound of claim 20 or a pharmaceutically acceptable salt thereof, wherein said F is $^{18}F$.

22. The compound of claim 1 or a pharmaceutically acceptable salt thereof, wherein R1 is selected from the group consisting of said positron emitting radionuclide selected from $^{11}C$, $^{13}N$, $^{15}O$, $^{52}Fe$, $^{55}Co$, $^{61}Cu$, $^{62}Cu$, $^{64}Cu$, $^{62}Zn$, $^{63}Zn$, $^{70}As$, $^{71}As$, $^{74}As$, $^{76}Br$, $^{79}Br$, $^{82}Rb$, $^{86}Y$, $^{89}Zr$, $^{110}In$, $^{120}I$, $^{124}I$, and $^{122}Xe$, said non-metal selected from $^{31}P$ and $^{13}C$, said lower alkyl substituted to contain a positron emitting radionuclide selected from $^{11}C$, $^{13}N$, $^{15}O$, $^{52}Fe$, $^{55}Co$, $^{61}Cu$, $^{62}Cu$, $^{64}Cu$, $^{62}Zn$, $^{63}Zn$, $^{70}As$, $^{71}As$, $^{74}As$, $^{76}Br$, $^{79}Br$, $^{82}Rb$, $^{86}Y$, $^{89}Zr$, $^{110}In$, $^{120}I$, $^{124}I$, and $^{122}Xe$, and said lower alkyl substituted to contain a non-metal selected from $^{31}P$ and $^{13}C$.

23. The compound of claim 1 or a pharmaceutically acceptable salt thereof, wherein R1 is said lower alkyl having 1 to 5 carbon atoms that is substituted to contain said halogen.

24. The compound of claim 1 or a pharmaceutically acceptable salt thereof, wherein R1 is hydroxyl and wherein said substituent of said heterocyclic ring is said halogen.

25. The compound of claim 24 or a pharmaceutically acceptable salt thereof, wherein said halogen is fluorine (F), chlorine (Cl), bromine (Br), iodine (I), or astatine (At).

26. The compound of claim 1 or a pharmaceutically acceptable salt thereof, wherein R1 is hydroxyl and said heterocyclic ring comprises said lower alkyl having 1 to 5 carbon atoms that is substituted to contain said halogen.

27. The compound of claim 26 or a pharmaceutically acceptable salt thereof, wherein said halogen is fluorine (F), chlorine (Cl), bromine (Br), iodine (I), or astatine (At).

28. The compound of claim 11 or a pharmaceutically acceptable salt thereof, wherein said positron emitting radionuclide is selected from $^{18}F$, $^{79}Br$, and $^{124}I$.

29. The compound of claim 1 or a pharmaceutically acceptable salt thereof, wherein R2, R3, or said heterocyclic ring comprises a lower alkyl having 1 to 5 carbon atoms substituted to contain a positron emitting radionuclide, wherein said positron emitting radionuclide is $^{11}C$, $^{13}N$, $^{15}O$, $^{18}F$, $^{52}Fe$, $^{55}Co$, $^{61}Cu$, $^{62}Cu$, $^{64}Cu$, $^{62}Zn$, $^{63}Zn$, $^{70}As$, $^{71}As$, $^{74}As$, $^{76}Br$, $^{79}Br$, $^{82}Rb$, $^{86}Y$, $^{89}Zr$, $^{110}In$, $^{120}I$, $^{124}I$, or $^{122}Xe$.

30. The compound of claim 10 or a pharmaceutically acceptable salt thereof, wherein said halogen is selected from fluorine (F), chlorine (Cl), bromine (Br), iodine (I), and astatine (At).

31. The compound of claim 9 or a pharmaceutically acceptable salt thereof, wherein R2, R3, or said heterocyclic ring comprises a lower alkyl substituted to contain a halogen.

32. The compound of claim 1 or a pharmaceutically acceptable salt thereof admixed with a pharmaceutically acceptable carrier or excipient.

33. The compound of claim 1, wherein said compound is in salt form with an anionic counterion.

34. The compound of claim 33, wherein said counterion is a halide.

35. The compound of claim 13 or a pharmaceutically acceptable salt thereof admixed with a pharmaceutically acceptable carrier or excipient.

36. The compound of claim 13, wherein said compound is in salt form with an anionic counterion.

37. The compound of claim 36, wherein said counterion is a halide.

38. The compound of claim 20 or a pharmaceutically acceptable salt thereof admixed with a pharmaceutically acceptable carrier or excipient.

39. The compound of claim 20, wherein said compound is in salt form with an anionic counterion.

40. The compound of claim 39, wherein said counterion is a halide.

41. The method of claim 14 or a pharmaceutically acceptable salt thereof, wherein said compound is admixed with a pharmaceutically acceptable carrier or excipient.

42. The method of claim 14, wherein said compound is in salt form with an anionic counterion.

43. The method of claim 42, wherein said counterion is a halide.

44. The method of claim 16, wherein R1 is hydroxyl and said substituent of said heterocyclic ring is said halogen.

45. The method of claim 16, wherein R1 is hydroxyl and said heterocyclic ring comprises a lower alkyl having 1 to 5 carbon atoms substituted to contain said halogen.

46. The method of claim 16, wherein said compound or a pharmaceutically acceptable salt thereof is admixed with a pharmaceutically acceptable carrier or excipient.

47. The method of claim 16, wherein said compound is in salt form with an anionic counterion.

48. The method of claim 47, wherein said counterion is a halide.

49. The compound of claim 1 or a pharmaceutically acceptable salt thereof, wherein R1 is hydrogen and at least one of R2, R3, or said heterocyclic ring comprises said substituent selected from said halogen.

50. The compound of claim 1 or a pharmaceutically acceptable salt thereof, wherein R1 is hydrogen and at least one of R2, R3, or said heterocyclic ring comprises said lower alkyl having 1 to 5 carbon atoms that is substituted to contain said halogen.

51. The method of claim 16, wherein R1 is hydrogen and at least one of R2, R3, or said heterocyclic ring comprises said substituent selected from said halogen.

52. The method of claim 16, wherein R1 is hydrogen and at least one of R2, R3, or said heterocyclic ring comprises said lower alkyl having 1 to 5 carbon atoms that is substituted to contain said halogen.

* * * * *